(12) United States Patent
Nakahata et al.

(10) Patent No.: US 10,588,549 B2
(45) Date of Patent: Mar. 17, 2020

(54) DRIVER'S PHYSICAL CONDITION DETECTION DEVICE AND METHOD

(71) Applicant: MAZDA MOTOR CORPORATION, Hiroshima (JP)

(72) Inventors: Youichiro Nakahata, Aki-gun (JP); Yohei Iwashita, Hiroshima (JP); Junichiro Kuwahara, Hiroshima (JP); Ryohei Hisamitsu, Hiroshima (JP)

(73) Assignee: MAZDA MOTOR CORPORATION, Hiroshima (JP)

( * ) Notice: Subject to any disclaimer, the term of this patent is extended or adjusted under 35 U.S.C. 154(b) by 280 days.

(21) Appl. No.: 15/683,039

(22) Filed: Aug. 22, 2017

(65) Prior Publication Data
US 2018/0056863 A1   Mar. 1, 2018

(30) Foreign Application Priority Data

Aug. 26, 2016  (JP) ................... 2016-166123

(51) Int. Cl.
| *A61B 5/18* | (2006.01) |
| *A61B 5/11* | (2006.01) |
| *B60Q 9/00* | (2006.01) |
| *B60R 11/04* | (2006.01) |
| *G01P 13/00* | (2006.01) |

(Continued)

(52) U.S. Cl.
CPC .......... *A61B 5/1128* (2013.01); *A61B 5/1114* (2013.01); *A61B 5/18* (2013.01); *B60Q 9/00* (2013.01); *B60R 11/04* (2013.01); *G01P 13/00* (2013.01); *G01P 15/0802* (2013.01); *B60R 2011/0028* (2013.01); *B60R 2300/8006* (2013.01); *B60W 2040/0818* (2013.01); *G06F 19/3418* (2013.01); *G16H 40/67* (2018.01)

(58) Field of Classification Search
CPC ................. A61B 5/18; A61B 5/1128
See application file for complete search history.

(56) References Cited

U.S. PATENT DOCUMENTS

2007/0008151 A1* 1/2007 Victor ............... A61B 5/11
                                                        340/573.1
2008/0114534 A1   5/2008 Yamazaki et al.
(Continued)

FOREIGN PATENT DOCUMENTS

| JP | 2005-080970 A | 3/2005 |
| JP | 2007-524134 A | 8/2007 |

(Continued)

OTHER PUBLICATIONS

JP Office Action dated Dec. 5, 2017, from corresponding JP Appl No. 2016-166123, with English translation, 4 pp.

*Primary Examiner* — Meredith Weare
(74) *Attorney, Agent, or Firm* — Studebaker & Brackett PC

(57) ABSTRACT

A driver's physical condition detection device for detecting a physical condition of a driver driving a vehicle includes a vehicle detector configured to detect a change in motion of the vehicle during driving, a driver detector configured to detect a change in motion of a head of the driver, and a physical condition determination portion configured to perform a determination process of determining whether or not the physical condition of the driver is deteriorated, based on the change in motion of the head of the driver with respect to the change in motion of the vehicle during driving.

5 Claims, 17 Drawing Sheets

(51) Int. Cl.
*G01P 15/08* (2006.01)
*G16H 40/67* (2018.01)
*B60W 40/08* (2012.01)
*B60R 11/00* (2006.01)
*G06F 19/00* (2018.01)

(56) References Cited

U.S. PATENT DOCUMENTS

| | | | | |
|---|---|---|---|---|
| 2012/0069301 | A1* | 3/2012 | Hirata | A61B 3/112 |
| | | | | 351/209 |
| 2016/0052391 | A1* | 2/2016 | Walsh | B60K 28/066 |
| | | | | 340/575 |
| 2017/0140232 | A1* | 5/2017 | Banno | G06T 7/70 |
| 2017/0161575 | A1* | 6/2017 | Banno | B60K 28/06 |
| 2018/0055438 | A1* | 3/2018 | Nakahata | A61B 5/1114 |

FOREIGN PATENT DOCUMENTS

| | | | |
|---|---|---|---|
| JP | 2007265377 A | * | 10/2007 |
| JP | 2015-021912 A | | 2/2015 |
| JP | 2016-009257 A | | 1/2016 |
| WO | 2006/072997 A1 | | 7/2006 |

* cited by examiner

FIG. 6
SECTION (A)
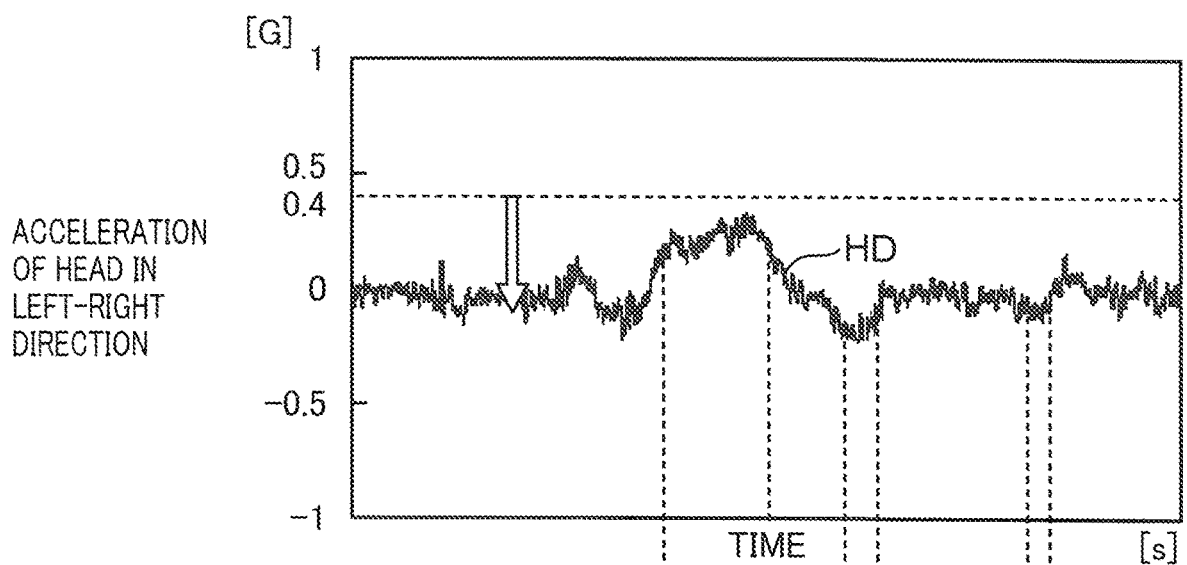
SECTION (B)
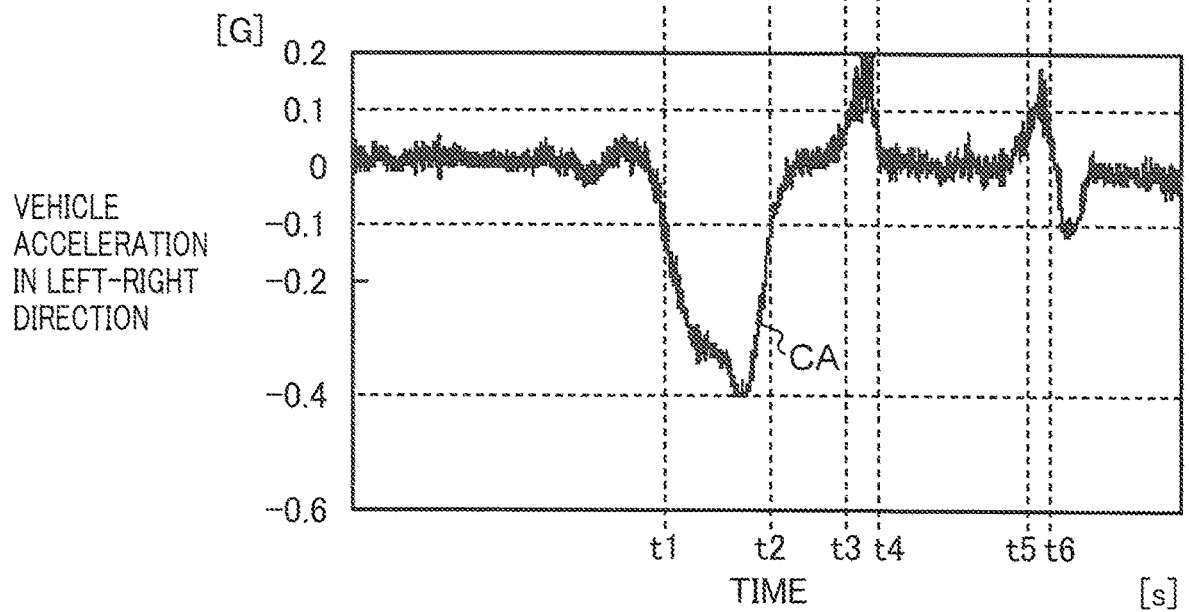

FIG. 7
SECTION (A)
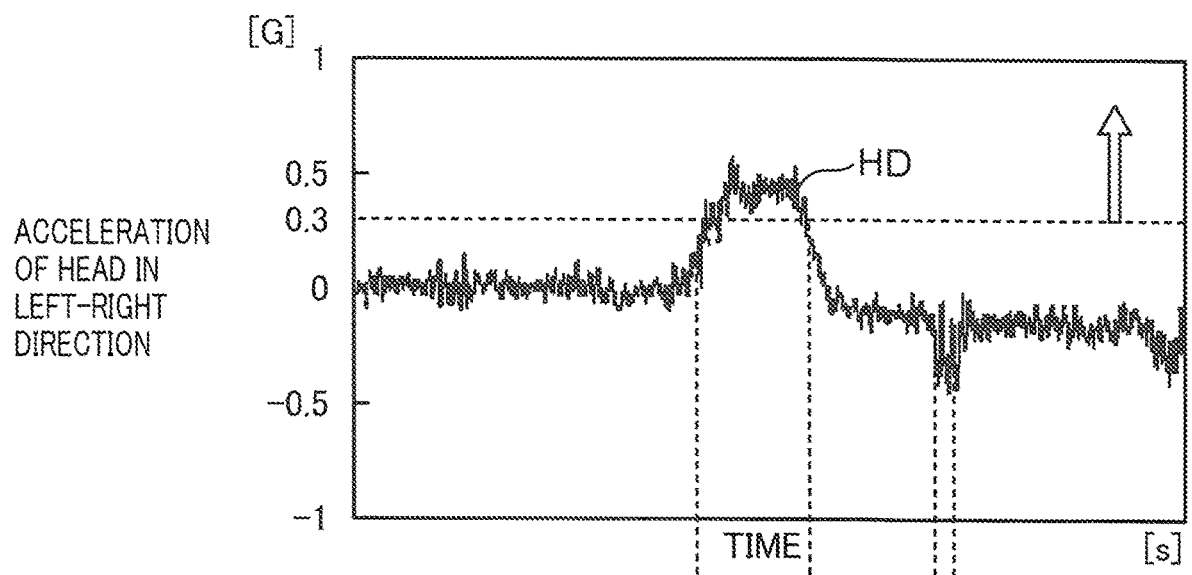
ACCELERATION OF HEAD IN LEFT-RIGHT DIRECTION
SECTION (B)
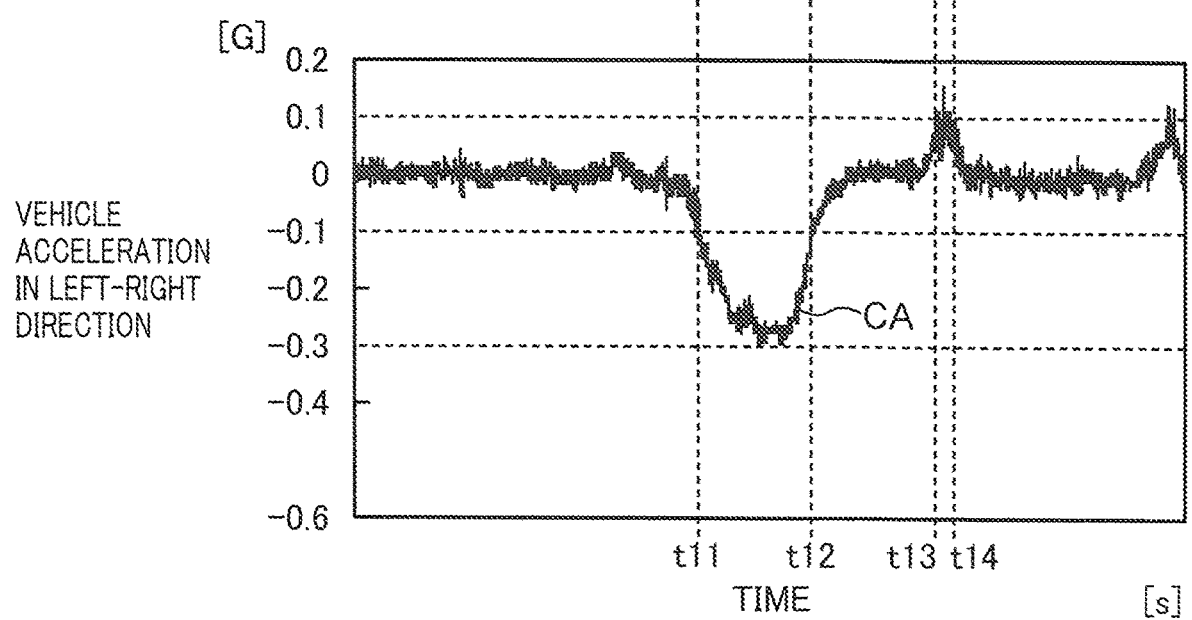
VEHICLE ACCELERATION IN LEFT-RIGHT DIRECTION

DRIVER'S PHYSICAL CONDITION DETECTION DEVICE AND METHOD

TECHNICAL FIELD

The technique disclosed herein relates to a driver's physical condition detection device and a method for detecting a physical condition of a driver.

BACKGROUND ART

As one of the causes of death by traffic accident, there is a sudden change in the physical condition of a driver during driving. A cause of the sudden change in the driver's physical condition includes various diseases such as cerebrovascular diseases and heart diseases. The condition of a driver who cannot continue driving by the sudden change in the physical condition is not constant. Conventionally, there is known a technique for detecting the sudden change in the driver's physical condition (see e.g. Japanese Unexamined Patent Publication No. 2015-021912). In the technique described in Japanese Unexamined Patent Publication No. 2015-021912, a deteriorated physical condition of a driver is estimated based on a driving position of the driver to detect a sign of deterioration of the physical condition.

Generally, it is often the case that by the time when a large change in the driving position of a driver appears, a deteriorated physical condition of the driver progresses to a certain extent. In order to secure safety of a driver, however, it is necessary to detect a deteriorated physical condition of the driver at an early stage before the deteriorated physical condition progresses.

SUMMARY OF THE INVENTION

The technique disclosed herein is directed to detecting a deteriorated physical condition of a driver at an early stage before the deteriorated physical condition progresses.

An aspect of the technique disclosed herein is directed to a driver's physical condition detection device for detecting a physical condition of a driver driving a vehicle. The driver's physical condition detection device includes: a vehicle detector configured to detect a change in motion of the vehicle during driving; a driver detector configured to detect a change in motion of a head of the driver; and a physical condition determination portion configured to perform a determination process of determining whether or not the physical condition of the driver is deteriorated, based on the change in motion of the head of the driver with respect to the change in motion of the vehicle during driving.

According to an aspect of the present disclosure, the determination process of determining whether or not the driver's physical condition is deteriorated is performed, based on a change in motion of a head of the driver with respect to a change in motion of the vehicle during driving. Therefore, it is possible to detect a deteriorated physical condition of a driver at an early stage before the deteriorated physical condition of the driver progresses.

These and other objects, features and advantages of the present invention will become more apparent upon reading the following detailed description along with the accompanying drawings.

BRIEF DESCRIPTION OF DRAWINGS

FIG. 1A to FIG. 2C are diagrams schematically illustrating an experiment result on an acceleration of a driver's head in a left-right direction of a vehicle, which changes, as the acceleration of the vehicle in the left-right direction changes;

FIG. 6 is a diagram schematically illustrating a change in the acceleration of a driver's head in a left-right direction of a vehicle with time, and a change in the acceleration of the vehicle in the left-right direction with time;

FIG. 7 is a diagram schematically illustrating a change in the acceleration of a driver's head in a left-right direction of a vehicle with time, and a change in the acceleration of the vehicle in the left-right direction with time;

DESCRIPTION OF EMBODIMENTS (Outline of Aspect of Present Disclosure)

First of all, an outline of an aspect of the present disclosure is described. As a result of conducting various experiments, the inventors of the present application found that there is a difference in a change of motion of a driver's head with respect to a change in motion of a vehicle between a case where a driver's physical condition is normal, and a case where a driver's physical condition is deteriorated.

Figure 2A:
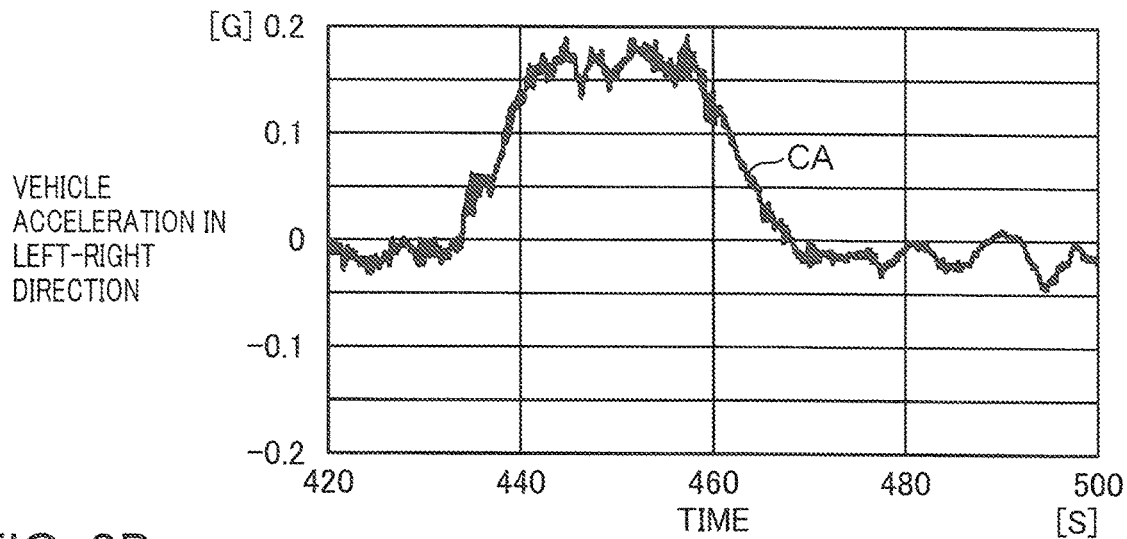
Figure 2B:
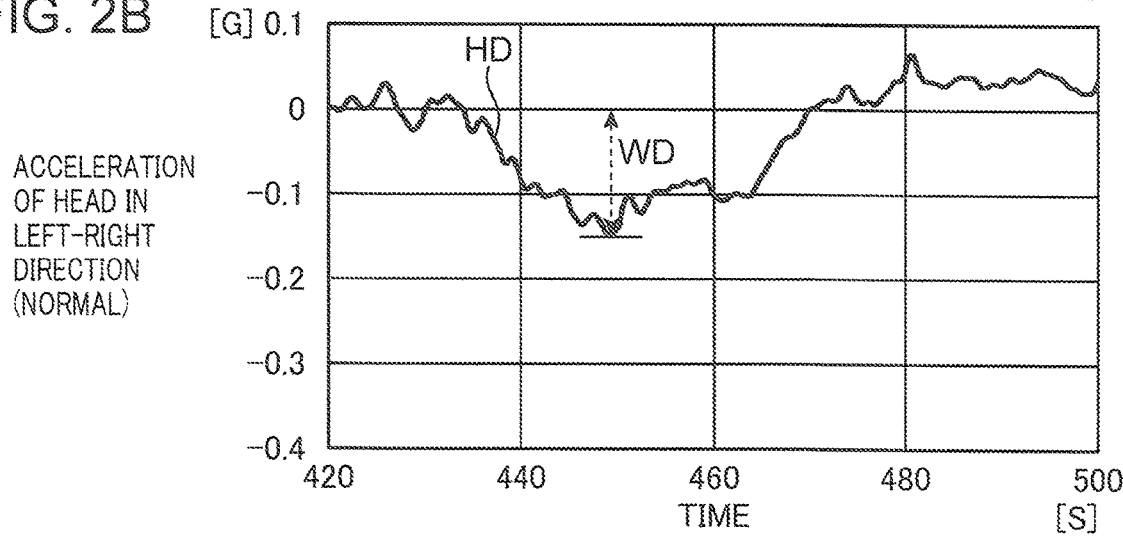
Figure 2C:
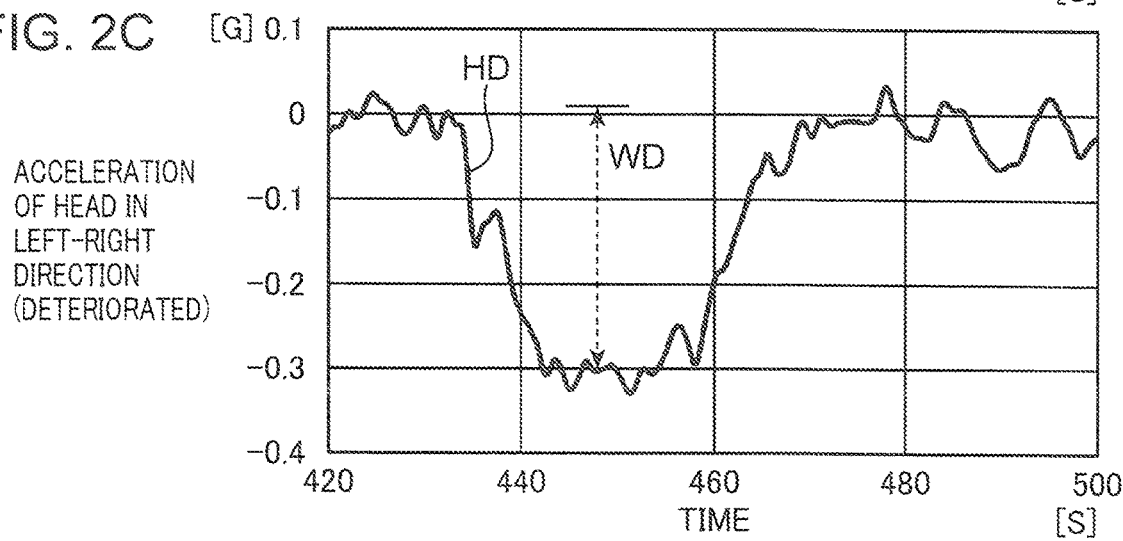

FIG. 2A to FIG. 2C are diagrams schematically illustrating an experiment result on an acceleration of a driver's head in a left-right direction of a vehicle, which changes, as the acceleration of the vehicle in the left-right direction changes. FIG. 2A illustrates a change in the acceleration of a vehicle in a left-right direction of the vehicle. FIG. 2B illustrates a change in the acceleration of a driver's head in the left-right direction when a driver's physical condition is normal. FIG. 2C illustrates a change in the acceleration of a driver's head in the left-right direction when a driver's physical condition is deteriorated. In FIG. 2A to FIG. 2C, the vertical axis denotes an acceleration [G], and the horizontal axis denotes a time [second].

In this example, "a left-right direction of a vehicle" is a direction orthogonal to a front-rear direction of the vehicle within a horizontal plane. In other words, "a left-right direction of a vehicle" is a direction orthogonal to a traveling direction of the vehicle travelling on a straight road within a horizontal plane. "A left-right direction of a vehicle" may also be referred to as "a vehicle width direction" or "a vehicle transverse direction". Note that in FIG. 2A, the acceleration changes in the plus direction, and in FIG. 2B and FIG. 2C, the accelerations change in the minus direction. This is due to a difference in determining the signs of acceleration, and an acceleration may be compared in terms of absolute values.

In FIG. 2A, an acceleration CA of a vehicle in a left-right direction of the vehicle increases in the range of from 0.15 to 0.2 [G] from a state of substantially 0 [G], and then, returns to a state of substantially 0 [G]. When a vehicle travelling on a straight road enters a curve, and returns to the straight road, the acceleration CA of the vehicle in the left-right direction shows a change as illustrated in FIG. 2A.

It is assumed that the acceleration CA of a vehicle in a left-right direction of the vehicle is directly exerted on a driver. In this case, as illustrated in FIG. 2B, a variation width WD of an acceleration HD of a driver's head in the left-right direction is about 0.1 [G] when a driver's physical condition is normal. On the other hand, as illustrated in FIG. 2C, a variation width WD of an acceleration HD of a driver's head in the left-right direction is about 0.3 [G] when a driver's physical condition is deteriorated.

Regarding the aforementioned difference, the inventors assume as follows. Specifically, a driver whose physical condition is normal predicts that the acceleration CA of a vehicle in a left-right direction of the vehicle may be exerted from the vehicle when the vehicle enters a curve, and tries to resist against the acceleration CA in the left-right direction, which may be exerted from the vehicle, with use of the muscles of the neck so that the head does not sway. As a result, the variation width WD of the acceleration HD of the driver's head in the left-right direction when a driver's physical condition is normal is substantially the same or slightly small, as compared with a variation width of the acceleration CA of the vehicle in the left-right direction, as illustrated in FIG. 2B.

On the other hand, when a driver's physical condition is deteriorated, the muscles of the neck may be weakened particularly, due to slight lowering of the consciousness. Therefore, it may be difficult for the driver to resist against the acceleration CA in the left-right direction, which may be exerted from the vehicle. As a result, the variation width WD of the acceleration HD of the driver's head in the left-right direction when a driver's physical condition is deteriorated is large, as compared with a variation width of the acceleration CA of the vehicle in the left-right direction, as illustrated in FIG. 2C.

Note that the experiment illustrated in FIG. 2A to FIG. 2C was conducted by letting a subject be seated on a front passenger seat in a state that the visual and audible sensations were deprived of in order to simulate a driver whose physical condition is deteriorated. The subject cannot predict that the acceleration CA in the left-right direction may be exerted from the vehicle when the vehicle enters a curve, because the subject's visual and audible sensations are deprived of. As a result, it may be difficult for the subject to resist against the acceleration CA in the left-right direction, which may be exerted from the vehicle, with use of the muscles of the neck. In this way, a driver whose physical condition is deteriorated, and whose muscles of the neck are weakened, is simulated.

In view of the aforementioned observation, the inventors found that it is possible to detect a deteriorated physical condition of a driver at an early stage by checking a change in motion of the driver's head with respect to a change in motion of a vehicle.

EMBODIMENTS

In the following, embodiments of the present disclosure are described with reference to the drawings. Note that in the drawings, same constituent elements are indicated by the same reference numerals, and repeated description thereof is omitted as necessary.

First Embodiment

Figure 1:
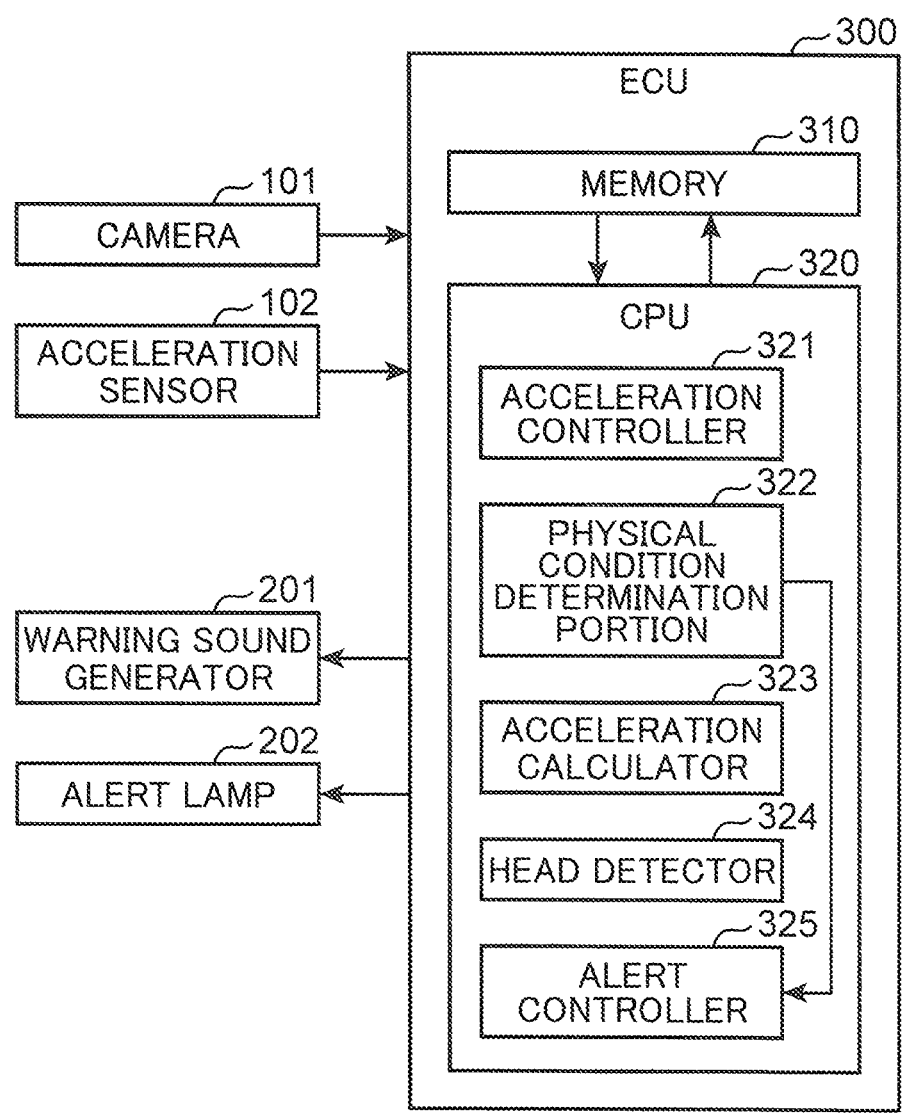
FIG. 1 is a block diagram schematically illustrating a configuration of a vehicle, in which a driver's physical condition detection device of a first embodiment is mounted.

FIG. 1 is a block diagram schematically illustrating a configuration of a vehicle, in which a driver's physical condition detection device of the first embodiment is mounted. A vehicle 10 is a four wheel vehicle, for instance. As illustrated in FIG. 1, the vehicle 10 includes a camera 101, an acceleration sensor 102, a warning sound generator 201, an alert lamp 202, and an electronic control unit (ECU) 300.

The camera 101 (an example of the driver detector) is mounted on a ceiling on the front side of a driver's seat in a passenger compartment of the vehicle 10, for instance, in such a manner that an optical axis of the camera 101 is directed toward the driver's seat in the vehicle 10. The camera 101 captures an image of the driver in the vehicle 10 from the front side to capture an image of the driver's head which moves in a left-right direction of the vehicle 10. The camera 101 outputs a captured frame image to the ECU 300 every 1/60 second, for instance. Alternatively, the camera 101 may be mounted on a ceiling above the driver's seat in a passenger compartment of the vehicle 10 in such a manner that an optical axis of the camera 101 is directed toward the driver's seat in the vehicle 10. Further alternatively, a plurality of cameras may be mounted on the ceiling of a passenger compartment of the vehicle 10 in such a manner that an optical axis of each of the cameras is directed toward the driver's seat in the vehicle 10. The camera 101 may be mounted in a passenger compartment of the vehicle 10 in such a manner that motion of the driver's head in a left-right direction of the vehicle 10 can be captured.

The acceleration sensor 102 (an example of the vehicle detector) detects an acceleration of the vehicle 10 in three axes directions perpendicular to each other, for instance. The acceleration sensor 102 outputs a detected acceleration of the vehicle 10 to the ECU 300. The warning sound generator 201 includes an electronic buzzer, for instance, and generates a warning sound to the driver. The alert lamp 202 includes a light emitting diode, for instance, and displays an alert to the driver. Note that the alert lamp 202 is not limited to a dedicated lamp, and may also be used as an alert lamp by causing a meter on an instrument panel or the like to blink.

The ECU 300 controls the overall operation of the vehicle 10. The ECU 300 includes a memory 310, a central processing unit (CPU) 320, and peripheral circuits. The memory 310 (an example of the storage) is constituted by a semiconductor memory such as a flash memory, a hard disk, or another storage element, for instance. The memory 310 includes a memory configured to store a program, and a memory configured to temporarily store data. The memory 310 may be constituted by a single memory having an area for storing a program, and an area for temporarily storing data.

The CPU 320 functions as an acceleration controller 321, a physical condition determination portion 322, an acceleration calculator 323, a head detector 324, and an alert controller 325 by being operated in accordance with a program stored in the memory 310.

The acceleration controller 321 acquires an acceleration of the vehicle 10 in a left-right direction of the vehicle 10 from acceleration data of the vehicle 10 in three axes directions perpendicular to each other, for instance, which is output from the acceleration sensor 102 every predetermined period (e.g. every 100 msec.). The acceleration controller 321 stores time data of the acceleration of the vehicle 10 in the left-right direction, which is obtained for a predetermined period (in the embodiment, e.g. for ten seconds) in the memory 310. When the predetermined period is ten seconds, for instance, and acceleration data is acquired from the acceleration sensor 102 every 100 msec., one hundred pieces of time data of the acceleration are stored in the memory 310.

The head detector 324 detects a driver's head by template matching from a frame image captured by the camera 101, for instance. The head detector 324 stores position coordinates of the center of the driver's head within an imaging area of the camera 101 in the memory 310 for each frame image, for instance. The head detector 324 stores time data of position coordinates of the driver's head for a predetermined period in the memory 310. When the predetermined period is one second, for instance, and a frame image is output from the camera 101 every 1/60 second, sixty pieces of time data of position coordinates of the driver's head are stored in the memory 310.

The acceleration calculator 323 calculates an acceleration of the driver's head in the left-right direction with use of time data of position coordinates of the driver's head, which is stored in the memory 310. For instance, the acceleration calculator 323 calculates a moving distance between frame images from position coordinates of the driver's head for each frame image, and calculates an acceleration from the amount of change of the calculated moving distance for each frame image. The acceleration calculator 323 stores time data of the acceleration of the driver's head for a predetermined period in the memory 310. As described above, when the predetermined period is one second, for instance, and a frame image is output from the camera 101 every 1/60 second, sixty pieces of time data of the acceleration of the driver's head are stored in the memory 310.

The physical condition determination portion 322 compares between an acceleration of the vehicle 10 in the left-right direction, and an acceleration of the driver's head in the left-right direction, and determines whether or not a driver's physical condition is deteriorated, based on the comparison result. Specifically, the physical condition determination portion 322 compares between a latest acceleration CAn out of time data of the acceleration CA of the vehicle 10 in the left-right direction, which is stored in the memory 310, and a latest acceleration HDn out of time data of an acceleration HD of the driver's head in the left-right direction, which is stored in the memory 310. The physical condition determination portion 322 determines that the driver's physical condition is deteriorated with use of a determination threshold value K1, when the latest acceleration HDn of the driver's head is larger than a value K1 times as large as the latest acceleration CAn of the vehicle 10. The determination threshold value K1 is determined in advance, and is stored in the memory 310. In the embodiment, for instance, K1=1. When the physical condition determination portion 322 determines that the driver's physical condition is deteriorated, the physical condition determination portion 322 notifies that the driver's physical condition is deteriorated to the alert controller 325.

The physical condition determination portion 322 determines whether or not a driver's physical condition is deteriorated only when an acceleration of the vehicle 10 in the left-right direction is not less than a predetermined acceleration threshold value ACth. This is because as far as the acceleration of the vehicle 10 in the left-right direction is small, there is no significant difference in the magnitude of the acceleration HD of the driver's head in the left-right direction between a case where a driver's physical condition is normal and a case where a driver's physical condition is deteriorated. As is clear from FIG. 2A to FIG. 2C, when the acceleration CA of the vehicle 10 in the left-right direction is in the range of from 0.15 [G] to 0.2 [G], there is a significant difference between a case where a driver's physical condition is normal and a case where a driver's physical condition is deteriorated. This means that it is possible to set the acceleration threshold value ACth to a value not larger than 0.15 [G] to 0.2 [G]. In the embodiment, for instance, ACth=0.1 [G].

When information that the driver's physical condition may be deteriorated is notified from the physical condition determination portion 322, the alert controller 325 activates the warning sound generator 201 and causes the alert lamp 202 to blink, to alert the driver. The alert controller 325 may activate a brake to decelerate or stop the vehicle 10, or may control a steering wheel to move the vehicle 10 to the edge of a road for instance, so as to support driving by the driver.

Figure 3:
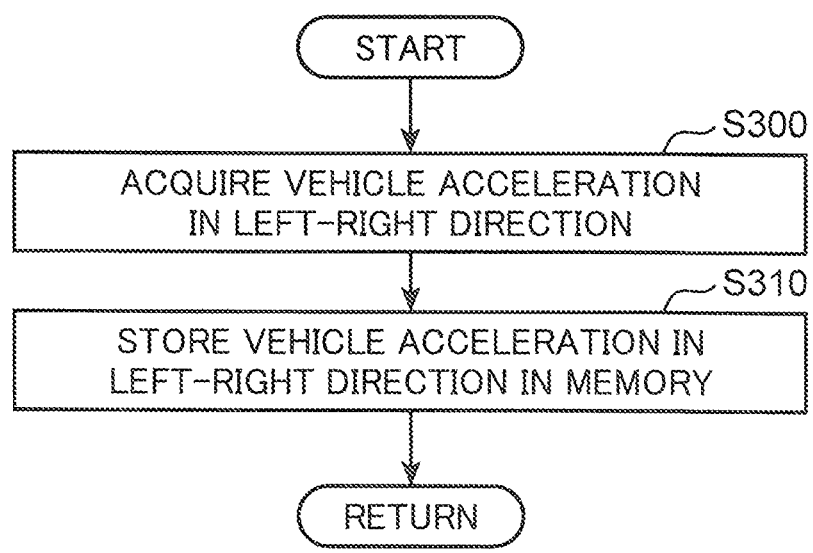
FIG. 3 is a flowchart schematically illustrating an example of a procedure of acquiring an acceleration of a vehicle in the driver's physical condition detection device of the first embodiment.

FIG. 3 is a flowchart schematically illustrating an example of a procedure of acquiring an acceleration of a vehicle in the driver's physical condition detection device of the first embodiment. The flow illustrated in FIG. 3 is executed every predetermined period (e.g. every 100 msec.). In step S300, the acceleration controller 321 acquires an acceleration of the vehicle 10 in the left-right direction from acceleration data of the vehicle 10 in three axes directions orthogonal to each other, for instance, which is output from the acceleration sensor 102. In step S310, the acceleration controller 321 stores time data of the acceleration of the vehicle 10 in the left-right direction for a predetermined period (in the embodiment, e.g. for ten seconds) in the memory 310. In other words, the acceleration controller 321 erases oldest acceleration data from the memory 310 when new acceleration data is obtained so that acceleration data for a predetermined period is stored in the memory 310. Thereafter, the process of FIG. 3 is terminated.

Figure 4:
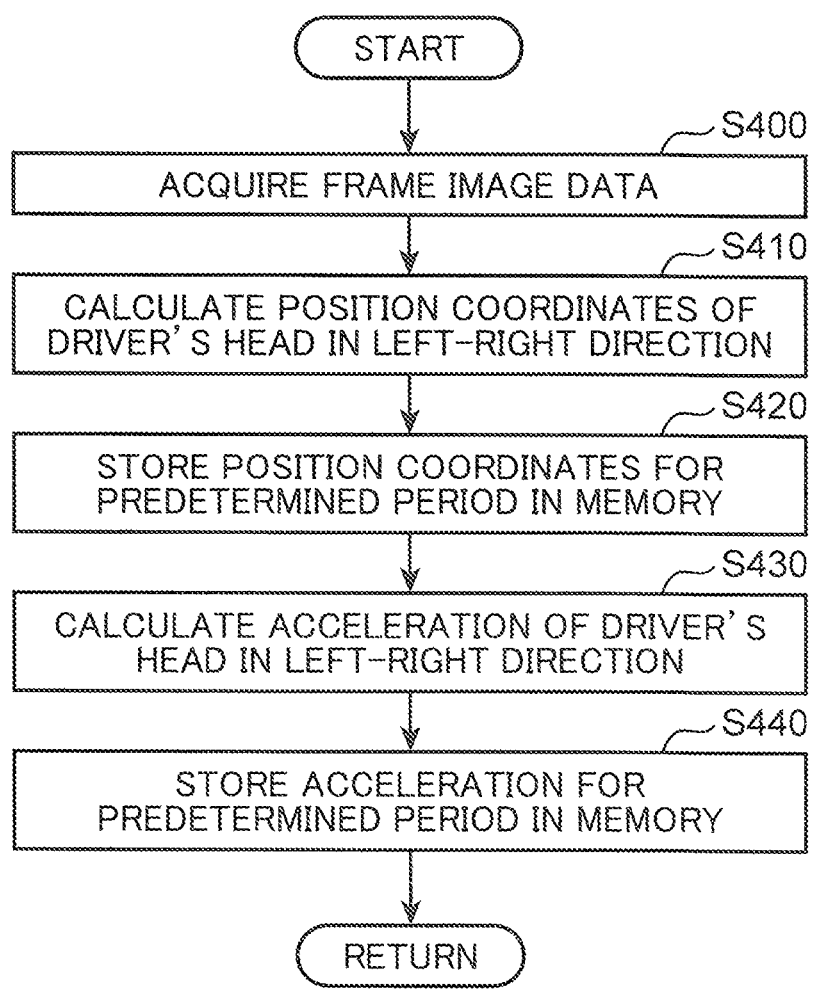
FIG. 4 is a flowchart schematically illustrating an example of a procedure of acquiring an acceleration of a driver's head in the driver's physical condition detection device of the first embodiment.

FIG. 4 is a flowchart schematically illustrating an example of a procedure of acquiring an acceleration of a driver's head in the driver's physical condition detection device of the first embodiment. The flow illustrated in FIG. 4 is executed every predetermined period (e.g. each time a frame image is output from the camera 101, namely, every 1/60 sec. in the embodiment).

In step S400, the head detector 324 acquires data of a frame image captured by the camera 101. In step S410, the head detector 324 detects a driver's head from an acquired frame image, and calculates position coordinates of the center of the driver's head, for instance. In step S420, the head detector 324 stores time data of position coordinates of the driver's head for a predetermined period in the memory 310 for each frame image. In other words, when new position coordinate data is acquired, the head detector 324 erases oldest position coordinate data from the memory 310, and stores position coordinate data for a predetermined period in the memory 310.

In step S430, the acceleration calculator 323 calculates an acceleration of the driver's head in the left-right direction with use of time data of position coordinates of the driver's head, which is stored in the memory 310. In step S440, the acceleration calculator 323 stores time data of the acceleration of the driver's head for a predetermined period in the memory 310. As well as step S420, when new acceleration data is acquired, the acceleration calculator 323 erases oldest acceleration data from the memory 310, and stores acceleration data for a predetermined period in the memory 310. Thereafter, the process of FIG. 4 is terminated.

Figure 5:
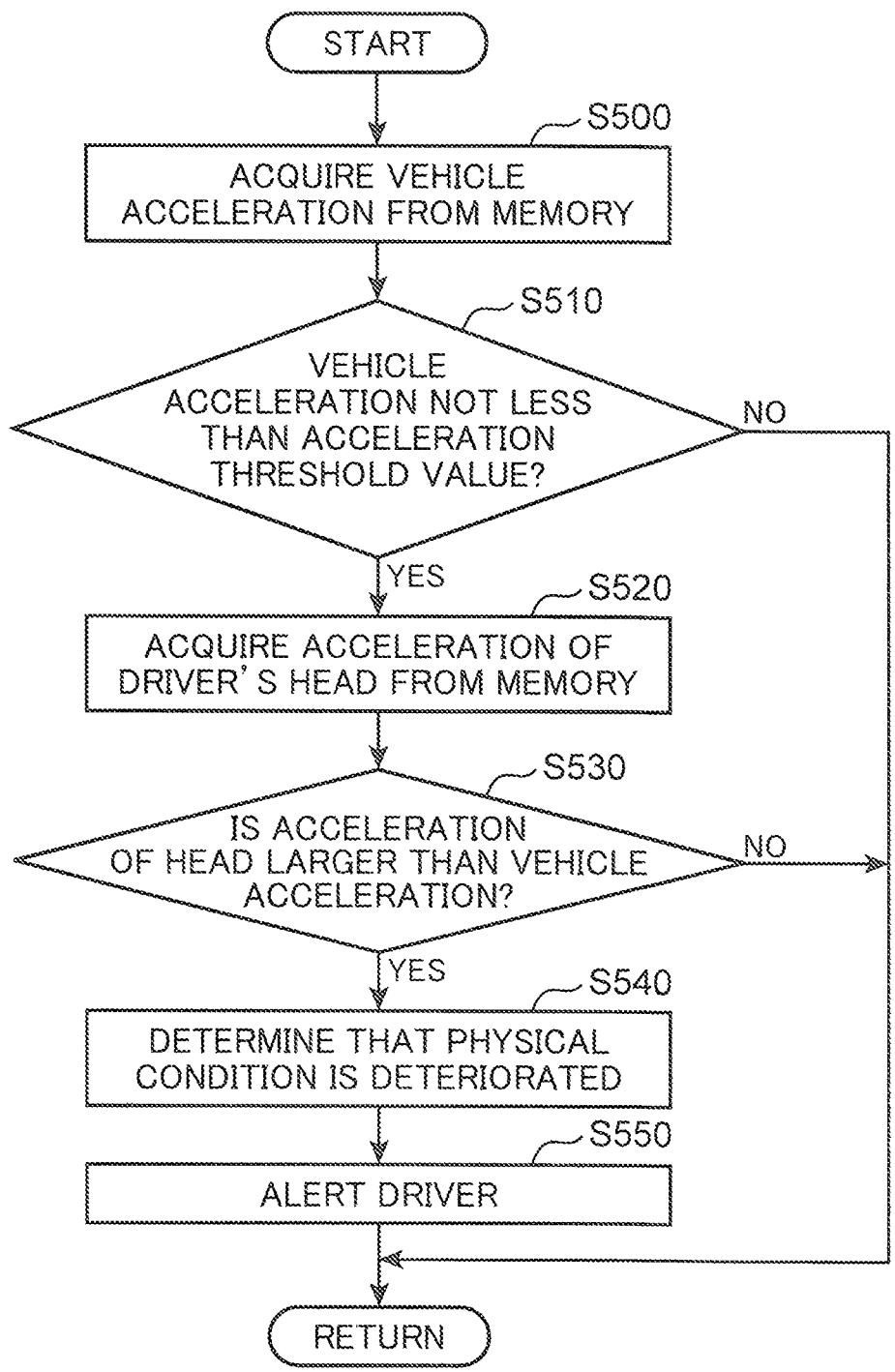
FIG. 5 is a flowchart schematically illustrating an example of a procedure of determining a driver's physical condition in the driver's physical condition detection device of the first embodiment.

FIG. 5 is a flowchart schematically illustrating an example of a procedure of determining a driver's physical condition in the driver's physical condition detection device of the first embodiment. The flow illustrated in FIG. 5 is executed every predetermined period (e.g. every 100 msec.).

FIG. 6 and FIG. 7 are diagrams schematically illustrating a change in the acceleration of a driver's head in the left-right direction with time, and a change in the acceleration of a vehicle in the left-right direction with time. In a section (A) and a section (B) of each of FIG. 6 and FIG. 7, the vertical axis denotes an acceleration [G], and the horizontal axis denotes a time [second].

The sections (A) of FIG. 6 and FIG. 7 illustrate time data of the acceleration of a driver's head in the left-right direction. The sections (B) of FIG. 6 and FIG. 7 illustrate time data of the acceleration of a vehicle in the left-right direction. The section (A) of FIG. 6 illustrates time data of the acceleration of a driver's head in the left-right direction when a driver's physical condition is normal. The section (A) of FIG. 7 illustrates time data of the acceleration of the driver's head in the left-right direction when a driver's physical condition is deteriorated.

In step S500 in FIG. 5, the physical condition determination portion 322 acquires the latest acceleration CAn out of time data of the acceleration of the vehicle 10 in the left-right direction, which is stored in the memory 310 (in the embodiment, e.g. data acquired for 10 seconds). In step S510, the physical condition determination portion 322 determines whether or not the absolute value of the acquired latest acceleration CAn of the vehicle in the left-right direction is not less than the acceleration threshold value ACth. When the absolute value of the latest acceleration CAn of the vehicle in the left-right direction is less than the acceleration threshold value ACth (NO in step S510), the process of FIG. 5 is terminated. On the other hand, when the absolute value of the latest acceleration CAn of the vehicle in the left-right direction is not less than the acceleration threshold value ACth (YES in step S510), the process proceeds to step S520.

As described above, in the embodiment, ACth=0.1 [G], for instance. Further, in the section (B) of FIG. 6 for instance, the time t1 is a point of time when the absolute value of the acceleration CA of a vehicle in the left-right direction becomes not less than 0.1 [G]. The time t2 is a point of time when the absolute value of the acceleration CA of the vehicle in the left-right direction becomes less than 0.1 [G] after the time t1. The time t3 is a point of time when the absolute value of the acceleration CA of the vehicle in the left-right direction becomes not less than 0.1 [G] after the time t2. The time t4 is a point of time when the absolute value of the acceleration CA of the vehicle in the left-right direction becomes less than 0.1 [G] after the time t3. The time t5 is a point of time when the absolute value of the acceleration CA of the vehicle in the left-right direction becomes not less than 0.1 [G] after the time t4. The time t6 is a point of time when the absolute value of the acceleration CA of the vehicle in the left-right direction becomes less than 0.1 [G] after the time t5.

Therefore, in the section (B) of FIG. 6 for instance, during a period from a measurement start time to the time t1, a judgment result in step S510 is NO, and the process of FIG. 5 is terminated. Thereafter, during a period from the time t1 to the time t2, during a period from the time t3 to the time t4, and during a period from the time t5 to the time t6, a judgement result in step S510 is YES, and the process proceeds to step S520.

Further, in the section (B) of FIG. 7 for instance, the time t11 is a point of time when the absolute value of the acceleration CA of a vehicle in the left-right direction becomes not less than 0.1 [G]. The time t12 is a point of time when the absolute value of the acceleration CA of the vehicle in the left-right direction becomes less than 0.1 [G] after the time t11. The time t13 is a point of time when the absolute value of the acceleration CA of the vehicle in the left-right direction becomes not less than 0.1 [G] after the time t12. The time t14 is a point of time when the absolute value of the acceleration CA of the vehicle in the left-right direction becomes less than 0.1 [G] after the time t13.

Therefore, in the section (B) of FIG. 7 for instance, during a period from a measurement start time to the time t11, a judgment result in step S510 is NO, and the process of FIG. 5 is terminated. Thereafter, during a period from the time t11 to the time t12, and during a period from the time t13 to the time t14, a judgement result in step S510 is YES, and the process proceeds to step S520.

Referring back to FIG. 5, in step S520, the physical condition determination portion 322 acquires a latest acceleration HDn out of time data of the acceleration of the driver's head in the left-right direction, which is stored in the memory 310, from the memory 310.

Subsequently, in step S530, the physical condition determination portion 322 determines whether or not the latest acceleration HDn of the driver's head is more than a value K1 times as large as the latest acceleration CAn of the vehicle. As described above, in the embodiment, K1=1. Therefore, the physical condition determination portion 322 determines whether or not the latest acceleration HDn of the driver's head is more than the latest acceleration CAn of the vehicle. When the latest acceleration HDn of the driver's head is not more than the latest acceleration CAn of the vehicle (NO in step S530), it is determined that the driver's physical condition is normal, and the process of FIG. 5 is terminated. On the other hand, when the latest acceleration HDn of the driver's head is more than the latest acceleration CAn of the vehicle (YES in step S530), the process proceeds to step S540.

In step S540, the physical condition determination portion 322 determines that the driver's physical condition is deteriorated, and notifies the alert controller 325 that the driver's physical condition is deteriorated. In step S550, the alert controller 325 activates the warning sound generator 201 and the alert lamp 202 to notify that the driver's physical condition is deteriorated to the driver. Thereafter, the process of FIG. 5 is terminated.

As described above, in the first embodiment, the physical condition determination portion 322 determines that the driver's physical condition is deteriorated when an acceleration of a driver's head in the left-right direction is more than a value K1 times as large as an acceleration of the vehicle in the left-right direction with use of the determination threshold value K1. When the driver's physical condition is deteriorated, the muscles of the neck are weakened due to slight lowering of the consciousness. Therefore, the acceleration of the driver's head in the left-right direction becomes larger than a value K1 times as large as the acceleration of the vehicle in the left-right direction. Thus, according to the first embodiment, it is possible to detect a deteriorated physical condition of a driver at an early stage before the deteriorated physical condition of the driver progresses.

Furthermore, in the first embodiment, the physical condition determination portion 322 determines whether or not a driver's physical condition is deteriorated only when an acceleration of the vehicle 10 in the left-right direction is not less than the predetermined acceleration threshold value ACth. Thus, according to the first embodiment, it is possible to accurately determine whether the driver's physical condition is good or bad.

Second Embodiment

Figure 8:
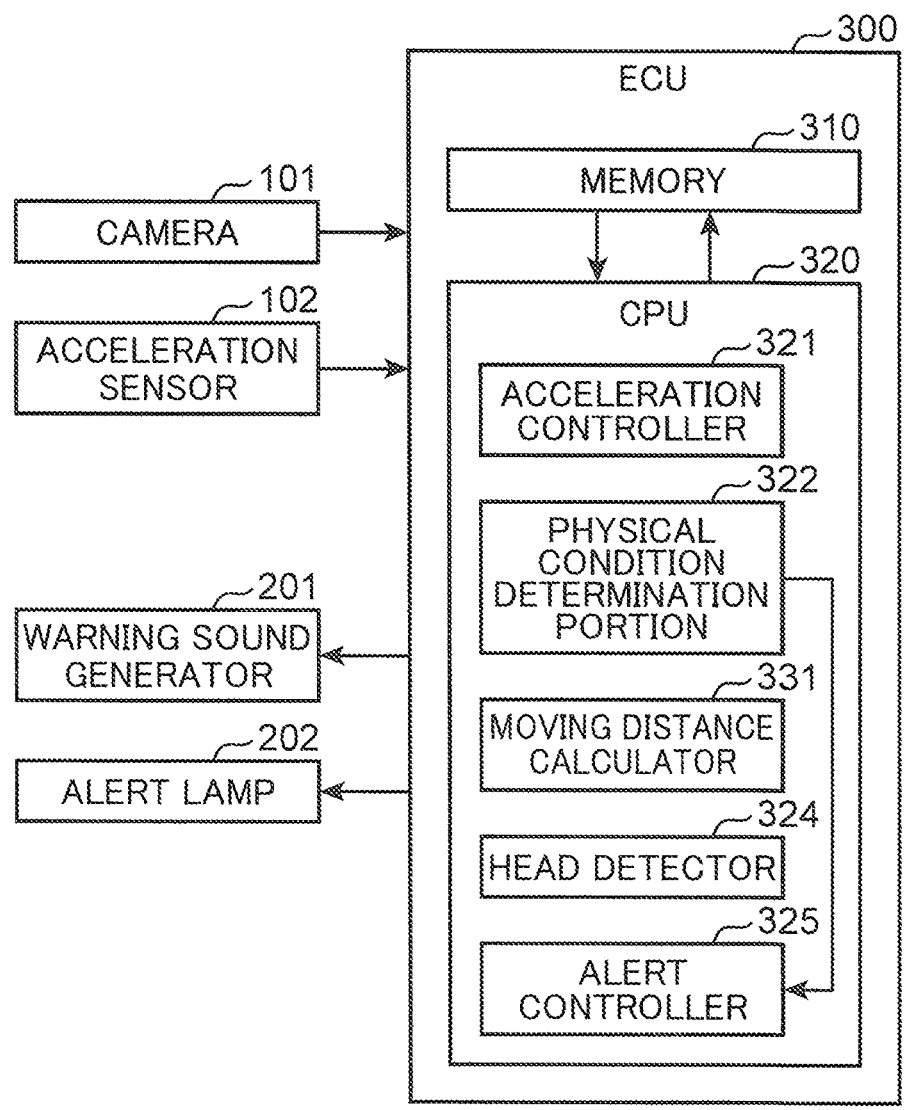
FIG. 8 is a block diagram schematically illustrating a configuration of a vehicle, in which a driver's physical condition detection device of a second embodiment is mounted.

FIG. 8 is a block diagram schematically illustrating a configuration of a vehicle, in which a driver's physical condition detection device of the second embodiment is mounted. In the first embodiment, a driver's physical condition is determined with use of an acceleration of a driver's head. In the second embodiment, a driver's physical condition is determined with use of a moving distance of a driver's head.

In the second embodiment, the CPU 320 functions as the acceleration controller 321, the physical condition determination portion 322, a moving distance calculator 331, the head detector 324, and the alert controller 325 by being operated in accordance with a program stored in the memory 310.

As with the first embodiment, the acceleration controller 321 acquires an acceleration of the vehicle 10 in a left-right direction of the vehicle 10 according to the procedure illustrated in FIG. 3 for instance, and stores time data of the acquired acceleration in the memory 310.

The moving distance calculator 331 calculates a moving distance of the driver's head in the left-right direction with use of time data of position coordinates of the driver's head, which is stored in the memory 310 by the head detector 324. The moving distance calculator 331 calculates a moving start position of the driver's head from position coordinates of the driver's head for each frame image. When the driver's head in a stationary state starts to move, the position where the driver's head is in a stationary state is set as a moving start position. Further, when the moving direction of the driver's head is reversed, the position where the moving direction is reversed is set as a moving start position.

The moving distance calculator 331 calculates a distance from the moving start position to the position where the driver's head is in a stationary state again, or to the position where the moving direction of the driver's head is reversed in the left-right direction. The moving distance calculator 331 stores the calculated moving distance in the memory 310, as the moving distance of the driver's head in the left-right direction.

Figure 9:
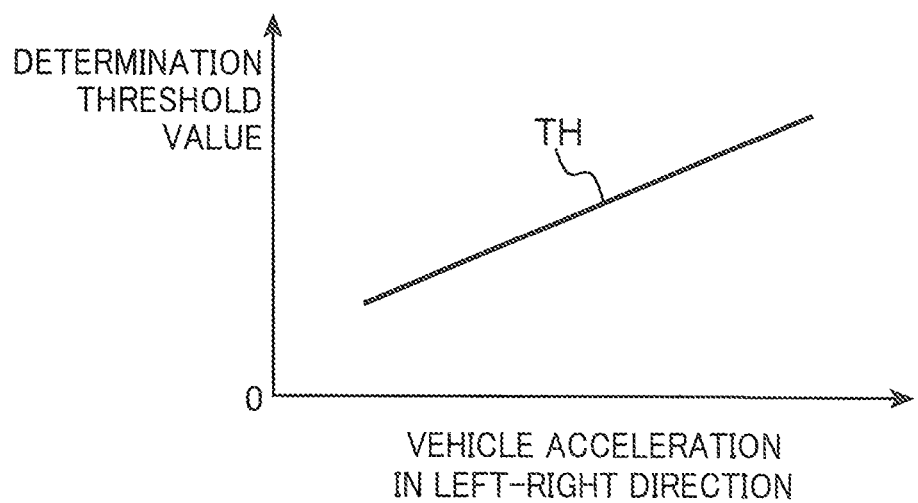
FIG. 9 is a diagram schematically illustrating an example of a determination threshold value.

The physical condition determination portion 322 determines that the driver's physical condition is deteriorated when the moving distance of the driver's head in the left-right direction is not less than a predetermined threshold value TH (see FIG. 9).

FIG. 9 is a diagram schematically illustrating, an example of the determination threshold value TH. In FIG. 9, the vertical axis denotes the determination threshold value TH, and the horizontal axis denotes an acceleration of a vehicle in a left-right direction of the vehicle. As illustrated in FIG. 9, the determination threshold value TH is determined in advance in such a manner that the determination threshold value TH increases, as the acceleration of the vehicle increases. The determination threshold value TH is stored in advance in the memory 310. It is possible to determine whether or not a driver's physical condition is deteriorated by using the determination threshold value TH as described above.

Note that, as illustrated in FIG. 9, the determination threshold value TH may not increase linearly, as the acceleration of the vehicle increases. For instance, the determination threshold value TH may stepwise increase, or exponentially increase, or logarithmically increase, as the acceleration of the vehicle increases. The memory 310 may store the determination threshold value TH illustrated in FIG. 9 as a look-up table.

Figure 10:
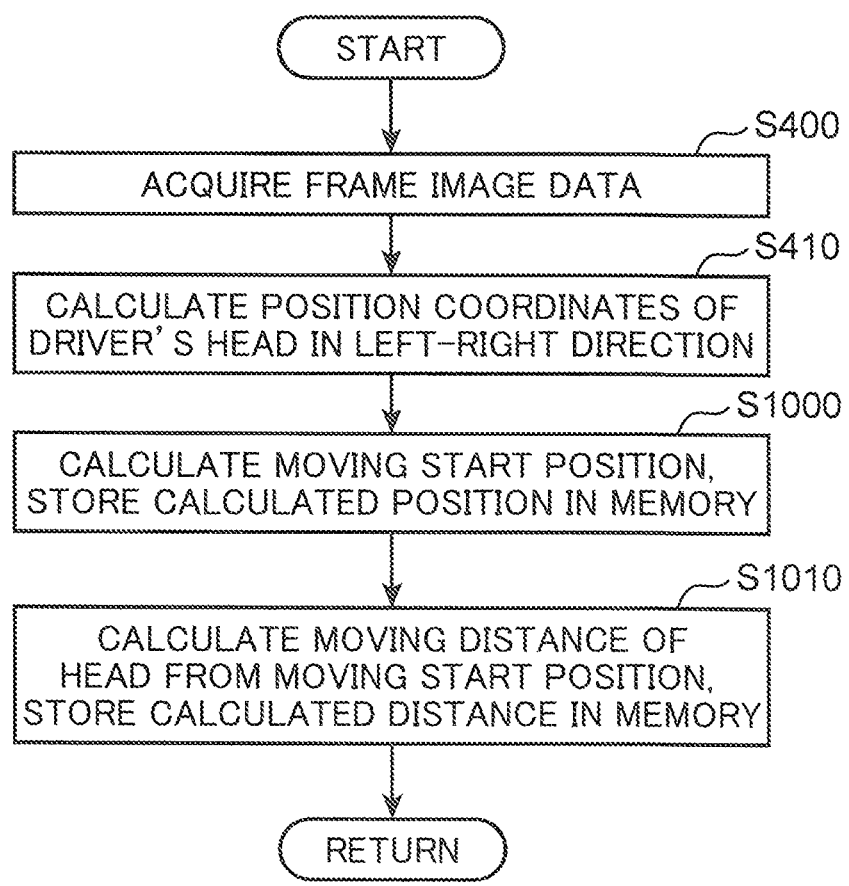
FIG. 10 is a flowchart schematically illustrating an example of a procedure of acquiring a moving distance of a driver's head in the driver's physical condition detection device of the second embodiment.

FIG. 10 is a flowchart schematically illustrating an example of a procedure of acquiring a moving distance of a driver's head in the driver's physical condition detection device of the second embodiment. The flow illustrated in FIG. 10 is executed every predetermined period (e.g. every 100 msec.).

Steps S400 and S410 in FIG. 10 are respectively the same as steps S400 and S410 in FIG. 4. In step S1000 following step S410, the moving distance calculator 331 calculates a moving start position of the driver's head in the left-right direction with use of time data of position coordinates of the driver's head, which is calculated in step S410, and stores the calculated moving start position in the memory 310. In step S1010, the moving distance calculator 331 calculates a moving distance of the driver's head from the moving start position in the left-right direction, and stores the calculated moving distance in the memory 310. Thereafter, the process of FIG. 10 is terminated.

Figure 11:
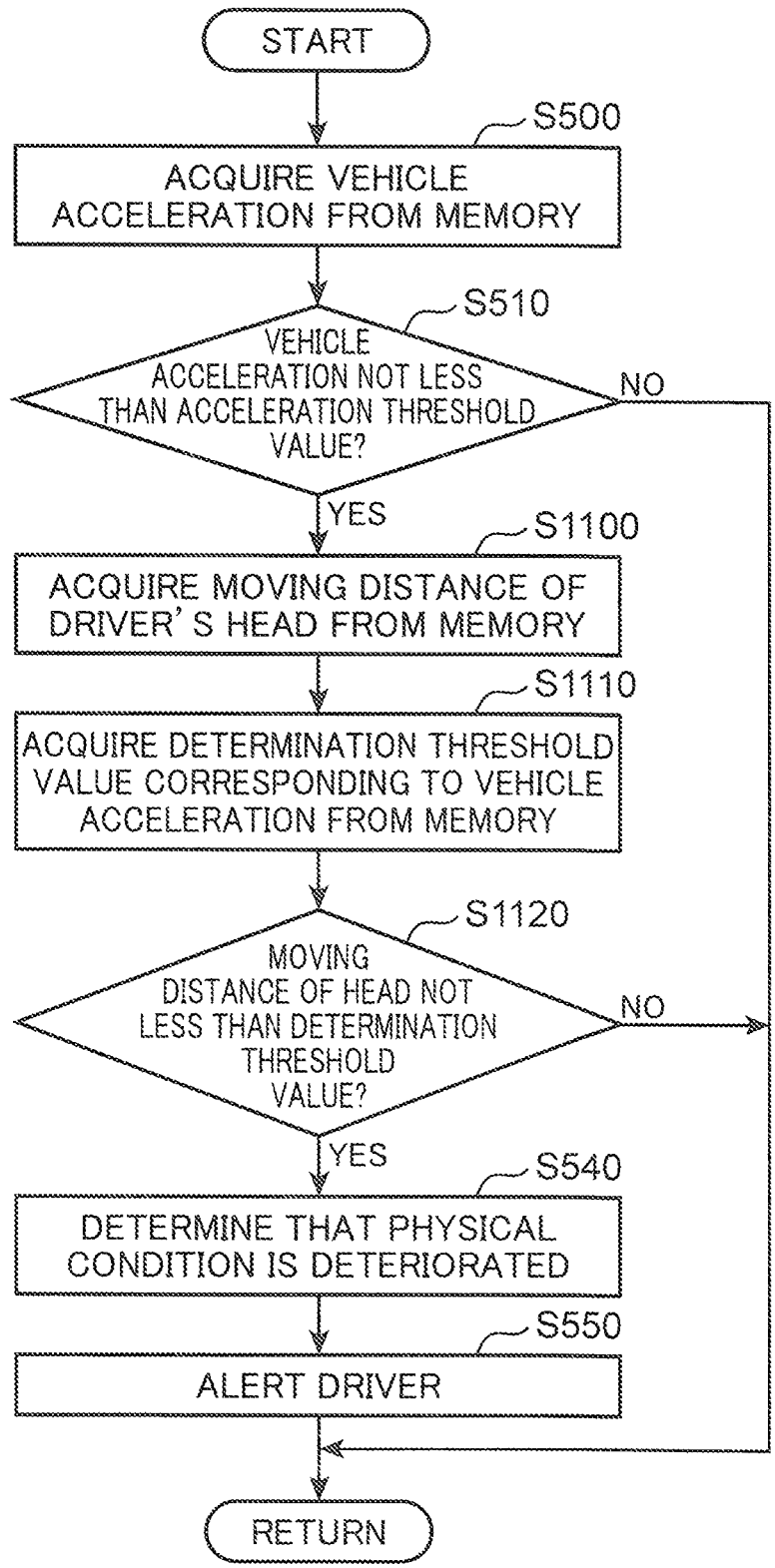
FIG. 11 is a flowchart schematically illustrating an example of a procedure of determining a driver's physical condition in the driver's physical condition detection device of the second embodiment.

FIG. 11 is a flowchart schematically illustrating an example of a procedure of determining a driver's physical condition in the driver's physical condition detection device of the second embodiment. The flow illustrated in FIG. 11 is executed every predetermined period (e.g. every 100 msec.).

Steps S500 and S510 in FIG. 11 are respectively the same as steps S500 and S510 in FIG. 5. When a latest acceleration CAn of a vehicle in the left-right direction is not less than the acceleration threshold value ACth (YES in step S510), the process proceeds to step S1100.

In step S1100, the physical condition determination portion 322 acquires, from the memory 310, a moving distance of the driver's head in the left-right direction, which is stored in the memory 310. Subsequently, in step S1110, the physical condition determination portion 322 acquires, from the memory 310, the determination threshold value TH associated with the acceleration of the vehicle acquired in step S500. Subsequently, in step S1120, the physical condition determination portion 322 determines whether or not the moving distance of the driver's head in the left-right direction is not less than the determination threshold value TH. When the moving distance of the driver's head in the left-right direction is less than the determination threshold value (NO in step S1120), the physical condition determination portion 322 determines that the driver's physical condition is normal, and the process of FIG. 11 is terminated. On the other hand, when the moving distance of the driver's head in the left-right direction is not less than the determination threshold value TH (YES in step S1120), the process proceeds to step S540. Steps S540 and S550 are respectively the same as steps S540 and S550 in FIG. 5.

As described above, in the second embodiment, the physical condition determination portion 322 determines that the driver's physical condition is deteriorated when the moving distance of the driver's head in the left-right direction is not less than the determination threshold value TH. When the driver's physical condition is deteriorated, the muscles of the neck are weakened due to slight lowering of the consciousness. This may increase the moving distance of the driver's head in the left-right direction. Thus, according to the second embodiment, it is possible to detect a deteriorated physical condition of a driver at an early stage before the deteriorated physical condition of the driver progresses.

Furthermore, in the second embodiment, the determination threshold value TH is determined in advance in such a manner that the determination threshold value TH increases, as the acceleration of the vehicle increases. When the acceleration of a vehicle increases, the moving distance of a driver's head in the left-right direction also increases. Thus, according to the second embodiment, it is possible to accurately determine whether the driver's physical condition is good or bad.

Third Embodiment

Figure 12:
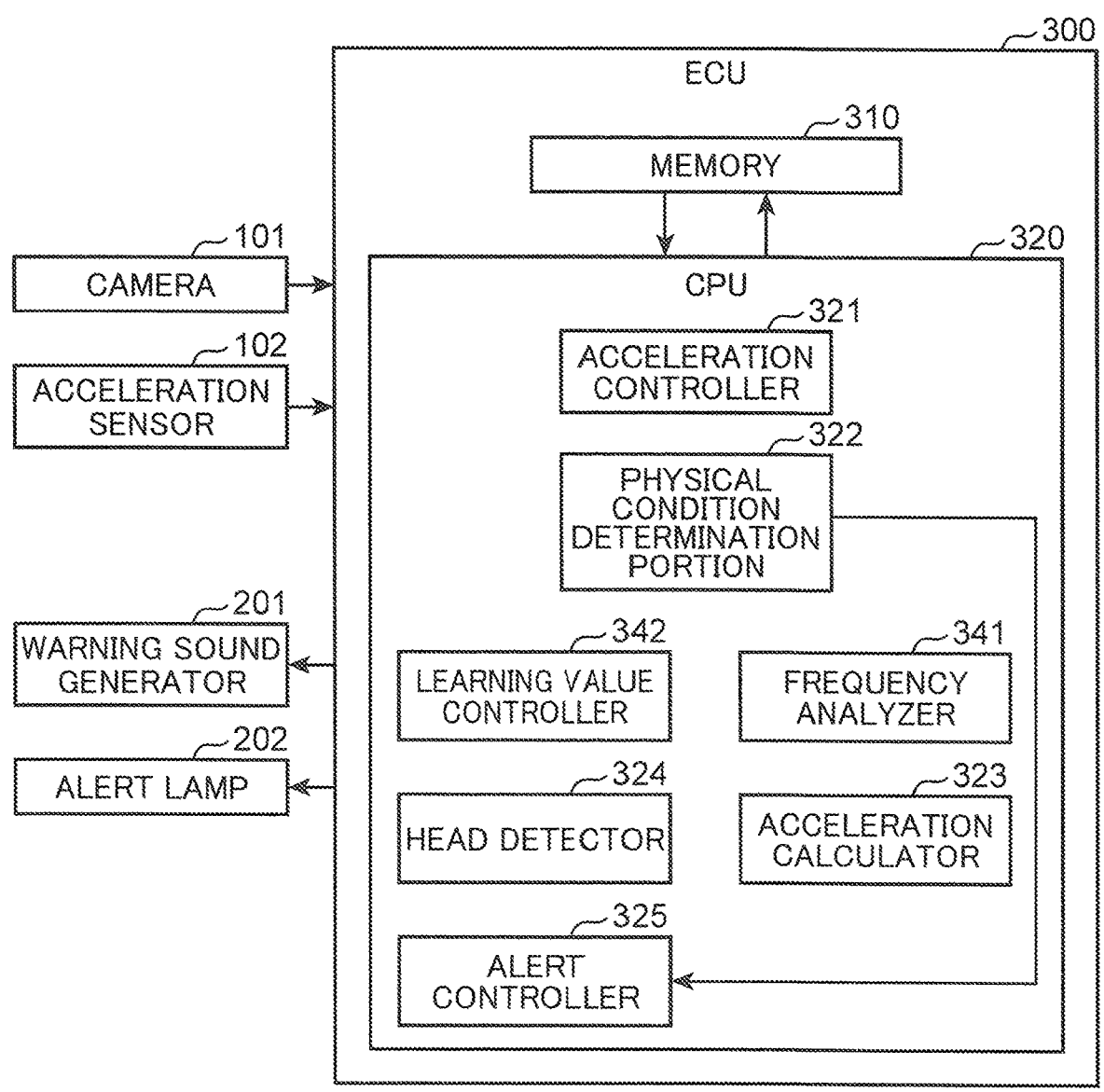
FIG. 12 is a block diagram schematically illustrating a configuration of a vehicle, in which a driver's physical condition detection device of a third embodiment is mounted.

FIG. 12 is a block diagram schematically illustrating a configuration of a vehicle, in which a driver's physical condition detection device of the third embodiment is mounted. In the first embodiment, a driver's physical condition is determined with use of an acceleration of a driver's head. In the third embodiment, a driver's physical condition is determined with use of a result of frequency analysis with respect to time data of the acceleration of a driver's head.

In the third embodiment, the CPU 320 functions as the acceleration controller 321, the physical condition determination portion 322, the acceleration calculator 323, the head detector 324, the alert controller 325, a frequency analyzer 341, and a learning value controller 342 by being operated in accordance with a program stored in a memory 310.

As with the first embodiment, the acceleration controller 321 acquires an acceleration of the vehicle 10 in a left-right direction of the vehicle 10 by the procedure illustrated in FIG. 3 for instance, and stores time data of the acquired acceleration in the memory 310.

As with the first embodiment, the acceleration calculator 323 calculates an acceleration of a driver's head in the left-right direction with use of time data of position coordinates of a driver's head, which is stored in the memory 310 by the head detector 324. As with the first embodiment, the acceleration calculator 323 stores, in the memory 310, time data of the acceleration of the driver's head for a predetermined period. In the third embodiment, the predetermined period is ten seconds, for instance.

The frequency analyzer 341 frequency-analyzes time data of the acceleration of the driver's head, which is stored in the memory 310 by the acceleration calculator 323, with use of a method such as a high-speed Fourier transformation for instance, and calculates frequency data of a power spectral density (PSD). The frequency analyzer 341 stores the calculated frequency data of the PSD in the memory 310.

Figure 13:
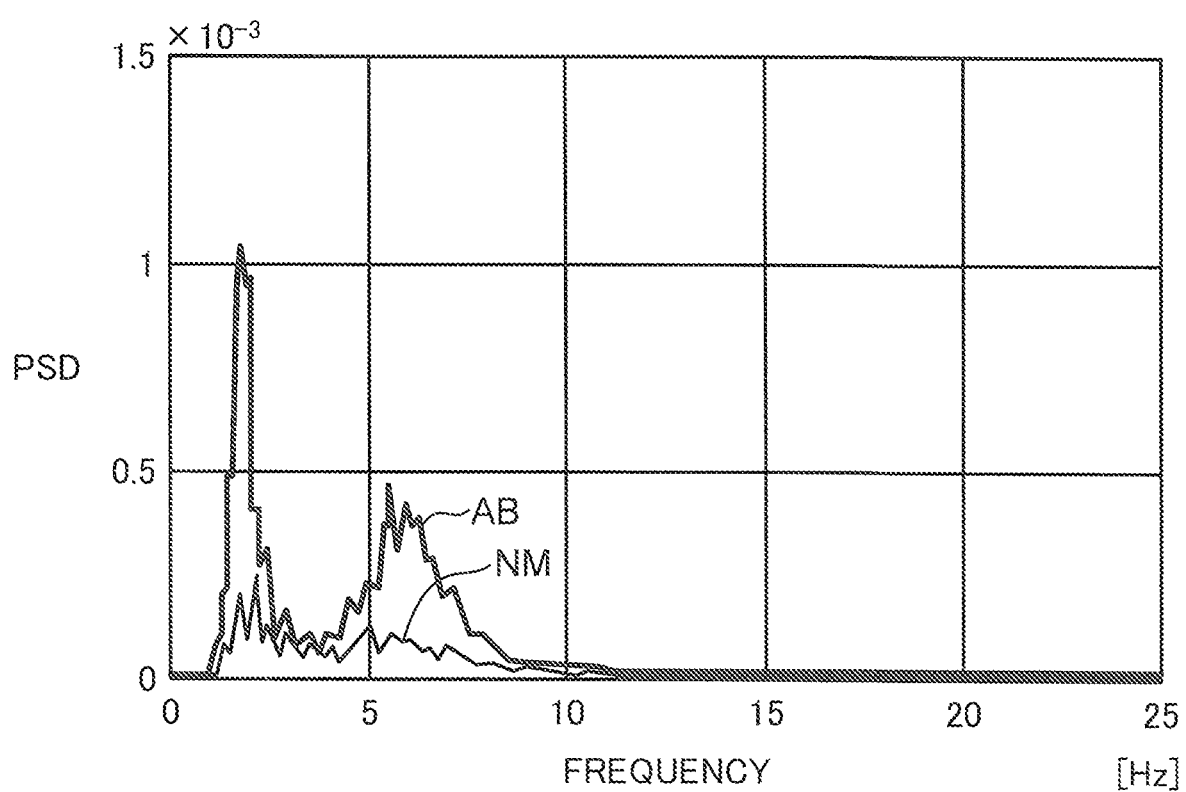
FIG. 13 is a diagram schematically illustrating an example of frequency data of a power spectral density (PSD), which is calculated by a frequency analyzer.

FIG. 13 is a diagram schematically illustrating an example of frequency data of the PSD, which is calculated by the frequency analyzer 341. In FIG. 13, the vertical axis denotes PSD, and the horizontal axis denotes a frequency [Hz]. Frequency data NM of PSD in FIG. 13 is data obtained by frequency-analyzing time data of the acceleration of a driver's head in the left-right direction when a driver's physical condition is normal, which is illustrated in the section (A) of FIG. 6 for instance. Frequency data AB of PSD in FIG. 13 is data obtained by frequency-analyzing time data of the acceleration of a driver's head in the left-right direction when a driver's physical condition is deteriorated, which is illustrated in the section (A) of FIG. 7 for instance.

As illustrated in FIG. 13, a maximum value (a peak value) of the frequency data AB of PSD when a driver's physical condition is deteriorated is large, as compared with a maximum value of the frequency data NM of PSD when a driver's physical condition is normal. In the third embodiment, the physical condition determination portion 322 determines whether the driver's physical condition is good or bad based on a difference between the maximum values.

Referring back to FIG. 12, the learning value controller 342 regards a period until a predetermined period elapses after an ignition switch of the vehicle 10 is turned on, as a period during which the driver's physical condition is normal, and stores an average value of maximum values of frequency data of the PSD, which are obtained for the aforementioned period in the memory 310, as a learned value.

The physical condition determination portion 322 compares between a maximum value of frequency data of the PSD, and a learned value stored in the memory 310, and determines whether or not a driver's physical condition is deteriorated based on the comparison result. Specifically, the physical condition determination portion 322 determines that the driver's physical condition is deteriorated when a maximum value of frequency data of the PSD is more than a value K2 times as large as a learned value. As is clear from FIG. 13, as far as K2 is a value from about 2 to 3, it is possible to determine whether or not a driver's physical condition is deteriorated. In view of the above, in the embodiment, K2=2.

Figure 14:
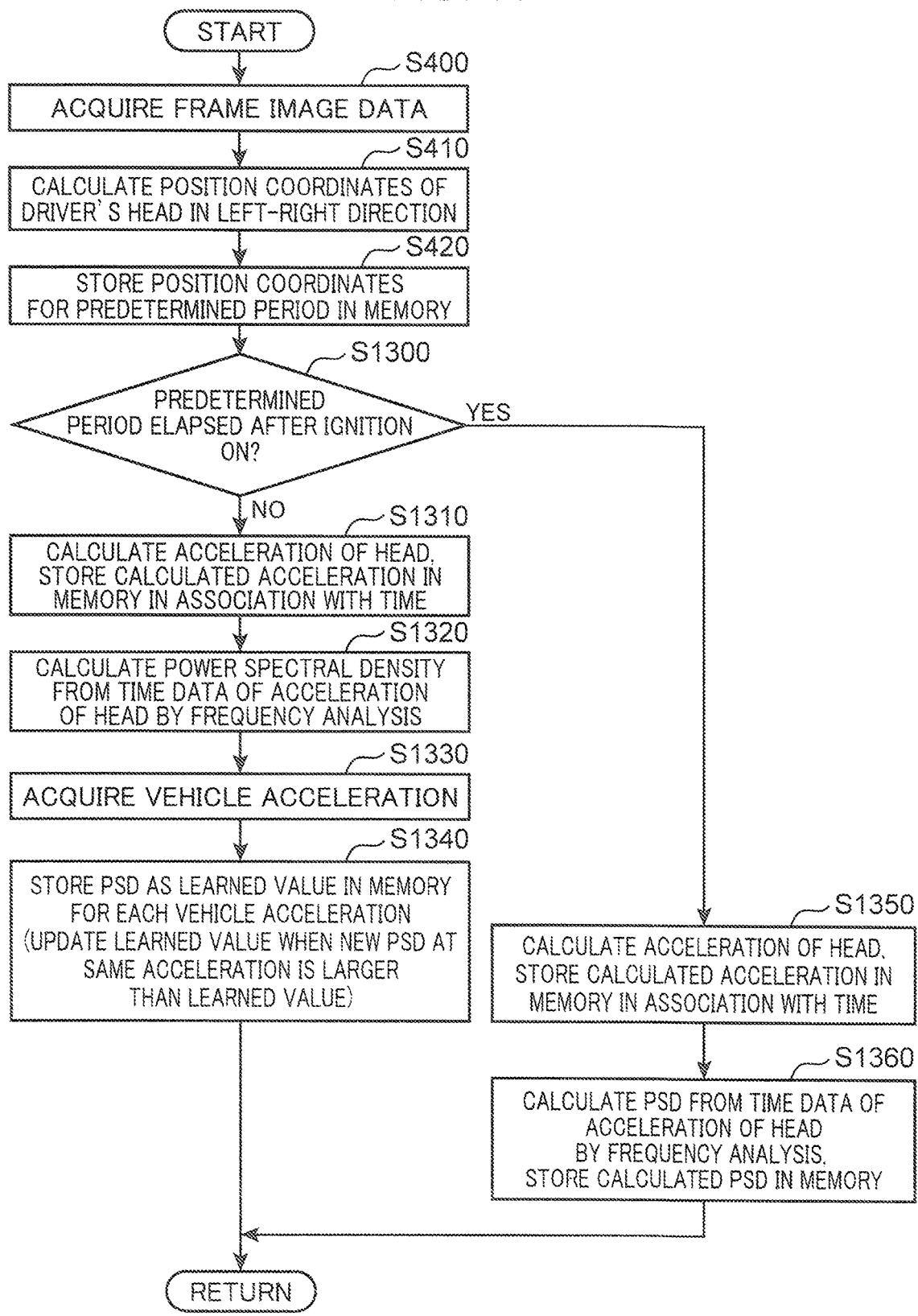
FIG. 14 is a flowchart schematically illustrating an example of a procedure of calculating frequency data of the PSD in the driver's physical condition detection device of the third embodiment.

FIG. 14 is a flowchart schematically illustrating an example of a procedure of calculating frequency data of the PSD in the driver's physical condition detection device of the third embodiment. The flow illustrated in FIG. 14 is executed every predetermined period (e.g. every 50 msec.). By executing the flow illustrated in FIG. 14 at a period of 50 msec. or less, it is possible to obtain frequency data of the PSD of 10 Hz or less, as illustrated in FIG. 13.

Steps S400, S410, and S420 in FIG. 14 are respectively the same as steps S400, S410, and S420 in FIG. 4. In step S1300 following step S420, the learning value controller 342 determines whether or not a predetermined period elapses after the ignition switch of the vehicle 10 is turned on.

When a predetermined period does not elapse after the ignition switch of the vehicle 10 is turned on (NO in step S1300), the process proceeds to step S1310. On the other hand, when a predetermined period elapses after the ignition switch of the vehicle 10 is turned on (YES in step S1300), the process proceeds to step S1350. Specifically, when a judgement result in step S1300 is NO, it is judged that the driver's physical condition is normal, and the process proceeds to step S1310 to perform a step of obtaining a learned value. On the other hand when a judgment result in step S1300 is YES, the process proceeds to step S1350 to perform a step of calculating a current acceleration.

In step S1310, the acceleration calculator 323 calculates an acceleration of the driver's head in the left-right direction with use of time data of position coordinates of the driver's head in the left-right direction, which is stored in the memory 310. The acceleration calculator 323 stores an acceleration for a predetermined period in the memory 310 in association with time.

In step S1320, the frequency analyzer 341 calculates frequency data of the PSD from time data of the acceleration of the driver's head, which is stored in the memory 310. In step S1330, the learning value controller 342 acquires an acceleration of the vehicle 10 in the left-right direction, which is stored in the memory 310.

In step S1340, the learning value controller 342 stores a maximum value of frequency data of the PSD in association with acceleration of the vehicle 10 in the memory 310 as a learned value. In this case, a maximum value of frequency data of the PSD is stored each time an acceleration of the vehicle 10 is acquired. Specifically, in acquiring new frequency data of the PSD, which is associated with a same acceleration of the vehicle 10, when a maximum value of new frequency data of the PSD is not larger than a stored learned value, the learning value controller 342 keeps the learned value as it is, and when a maximum value of new frequency data of the PSD is larger than a stored learned value, the learned value is updated by the maximum value of new frequency data of the PSD. Thereafter, the process of FIG. 14 is terminated.

In step S1350, the acceleration calculator 323 calculates an acceleration of the driver's head in the left-right direction with use of time data of position coordinates of the driver's head in the left-right direction, which is stored in the memory 310. The acceleration calculator 323 stores an acceleration for a predetermined period in the memory 310 in association with time. In step S1360, the frequency analyzer 341 calculates frequency data of the PSD from time data of the acceleration of the driver's head, which is stored in the memory 310. The frequency analyzer 341 stores a maximum value of the calculated frequency data of the PSD in the memory 310. Thereafter, the process of FIG. 14 is terminated.

Figure 15:
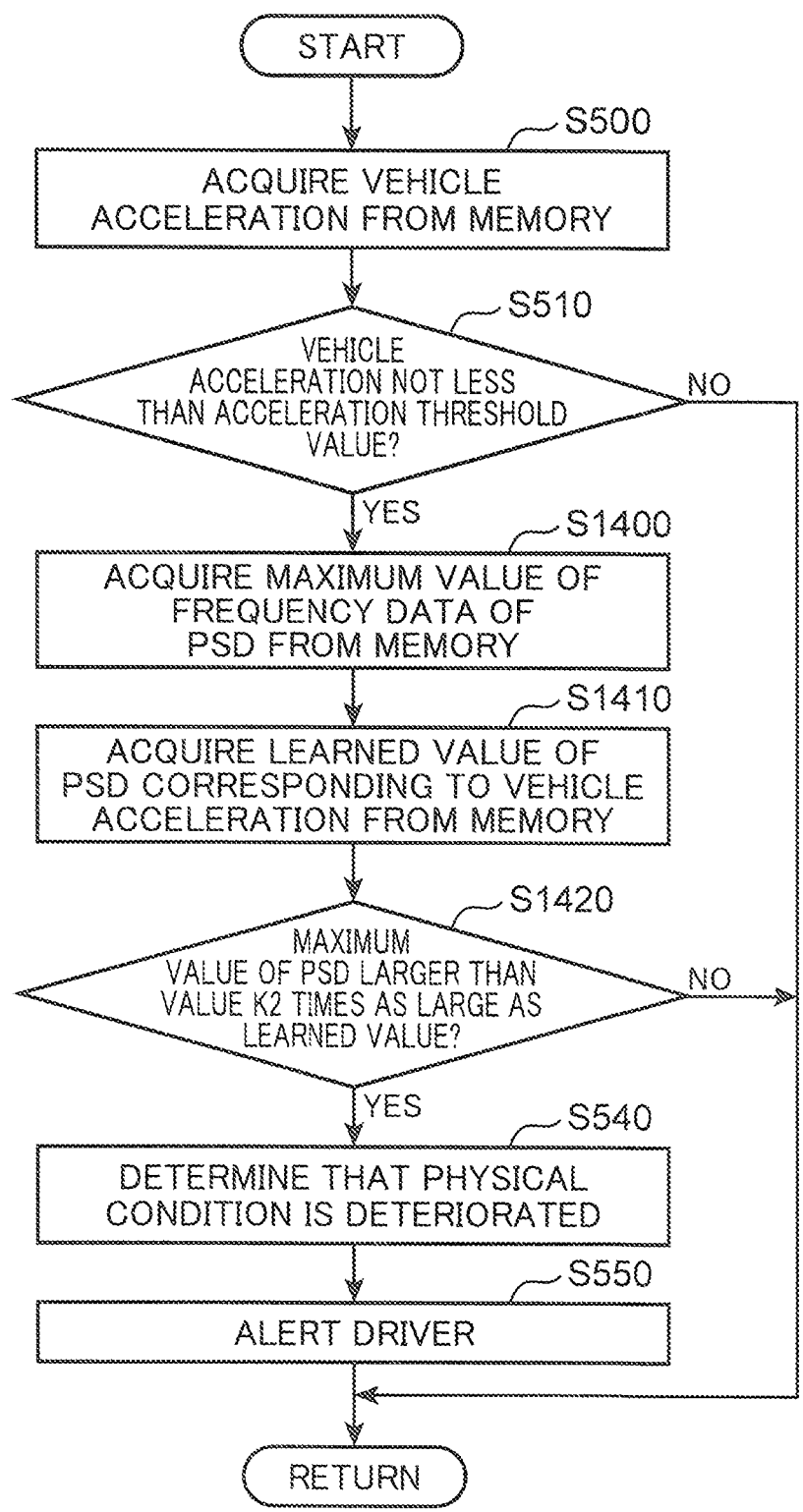
FIG. 15 is a flowchart schematically illustrating an example of a procedure of determining a driver's physical condition in the driver's physical condition detection device of the third embodiment.

FIG. 15 is a flowchart schematically illustrating an example of a procedure of determining a driver's physical condition in the driver's physical condition detection device of the third example embodiment. The flow illustrated in FIG. 15 is executed every predetermined period (e.g. every 100 msec.).

Steps S500 and S510 in FIG. 15 are respectively the same as steps S500 and S510 in FIG. 5. When a latest acceleration CAn of the vehicle in the left-right direction is not less than the acceleration threshold value ACth (YES in step S510), the process proceeds to step S1400.

In step S1400, the physical condition determination portion 322 acquires a maximum value (a peak value) of frequency data of the PSD, which is stored in the memory 310. In step S1410, the physical condition determination portion 322 acquires, from the memory 310, a learned value of frequency data of the PSD, which is associated with the acceleration of the vehicle 10 acquired in step S500.

In step S1420, the physical condition determination portion 322 determines whether or not the maximum value of frequency data of the PSD is not less than a value K2 times as large as a learned value of frequency data of the PSD. When the maximum value of frequency data of the PSD is not larger than a value K2 times as large as the learned value of frequency data of the PSD (NO in step S1420), the process of FIG. 15 is terminated. When the maximum value of frequency data of the PSD is larger than a value K2 times as large as the learned value of frequency data of the PSD (YES in step S1420), the process proceeds to step S540. Steps S540 and S550 are respectively the same as steps S540 and S550 in FIG. 5.

As described above, in the third embodiment, the frequency analyzer 341 calculates frequency data of the PSD from time data of the acceleration of a driver's head in the left-right direction. The physical condition determination portion 322 determines that the driver's physical condition is deteriorated when a maximum value of frequency data of the PSD is larger than a value K2 times as large as a learned value. When the driver's physical condition is deteriorated, the muscles of the neck are weakened due to slight lowering of the consciousness. As a result, a maximum value of frequency data of the PSD, which is obtained by frequency-analyzing time data of the acceleration of a driver's head in the left-right direction, is small, as compared with a case where the driver's physical condition is normal. Thus, according to the third embodiment, it is possible to detect a deteriorated physical condition of a driver at an early stage before the deteriorated physical condition of the driver progresses.

Furthermore, in the third embodiment, the learning value controller 342 regards a period until a predetermined period elapses after the ignition switch of the vehicle 10 is turned on, as a period during which the driver's physical condition is normal, and stores an average value of maximum values of frequency data of the PSD, which are obtained for the aforementioned period in the memory 310, as a learned value. In this way, a learned value is obtained each time the ignition switch of the vehicle 10 is turned on. Therefore, it is possible to obtain a learned value appropriate for the driver. Thus, according to the third embodiment, it is possible o accurately determine whether the driver's physical condition is good or bad.

Note that in the third embodiment, frequency data of the PSD is compared with a learned value. The embodiment, however, is not limited to the above. For instance, frequency data of the PSD may be compared with a determination threshold value determined in advance.

Figure 16:
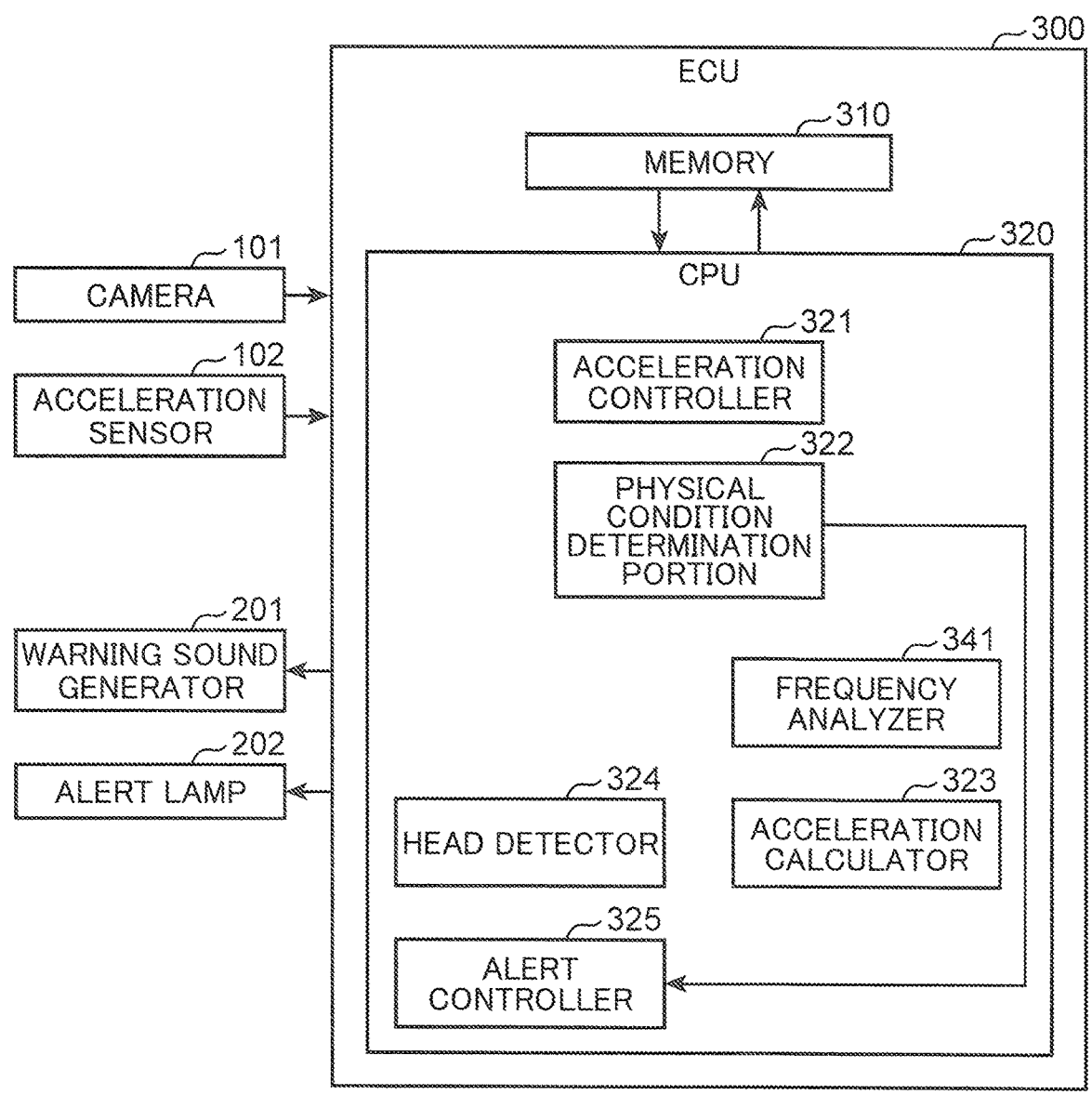
FIG. 16 is a block diagram schematically illustrating another configuration of the vehicle, in which the driver's physical condition of the third embodiment is mounted, which is different from the configuration illustrated in FIG. 12.

FIG. 16 is a block diagram schematically illustrating another configuration of the vehicle, in which the driver's physical condition detection device of the third embodiment is mounted, which is different from the configuration illustrated in FIG. 12. The CPU 320 illustrated in FIG. 16 does not include the learning value controller 342, which is provided in the CPU 320 illustrated in FIG. 12.

The physical condition determination portion 322 in FIG. 16 determines that the driver's physical condition is deteriorated when a maximum value of frequency data of the PSD is larger than a determination threshold value stored in advance in the memory 310. The determination threshold value may be obtained in advance by an experiment, for instance, and may be stored in the memory 310. In the third embodiment, as illustrated in FIG. 9, the determination threshold value is set in such a manner that the determination threshold value increases, as the acceleration of the vehicle increases. Note that in the example illustrated in FIG. 13, the determination threshold value may be set to a fixed value in the vicinity of $0.5 \times 10^{-3}$, for instance. By using the determination threshold value as described above, it is possible to determine whether or not a driver's physical condition is deteriorated.

Figure 17:
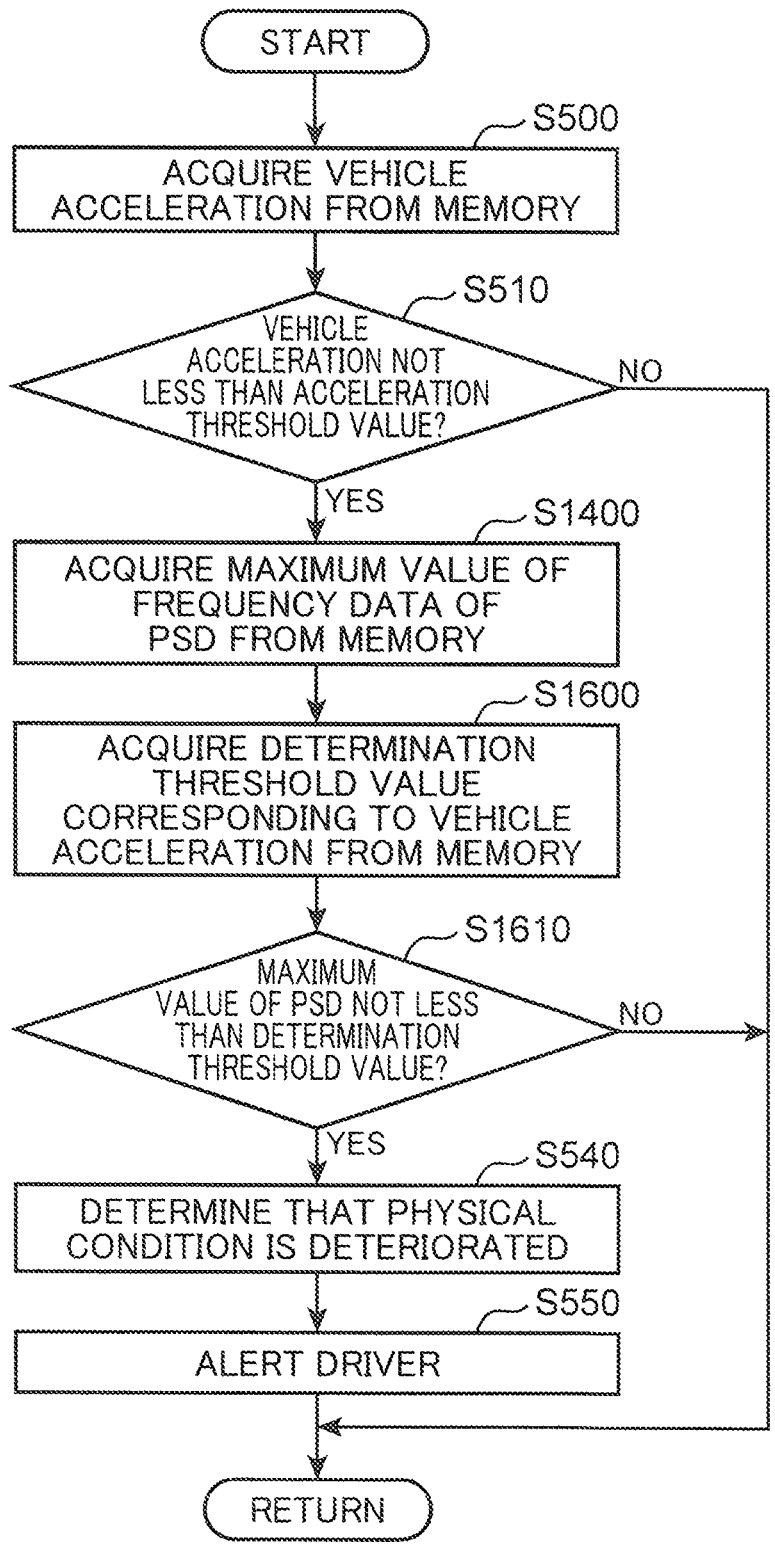
FIG. 17 is a flowchart schematically illustrating an example of a procedure of determining, a driver's physical condition in the configuration illustrated in FIG. 16.

FIG. 17 is a flowchart schematically illustrating an example of a procedure of determining a driver's physical condition in the configuration illustrated in FIG. 16. The flow illustrated in FIG. 17 is executed every predetermined period (e.g. every 100 msec.).

Steps S500 and S510 in FIG. 17 are respectively the same as steps S500 and S510 in FIG. 5. Step S1400 in FIG. 17 is the same as step S1400 in FIG. 15. In step S1600 following step S1400, the physical condition determination portion 322 acquires, from the memory 310, the determination threshold value associated with an acceleration of the vehicle 10 acquired in step S500.

In step S1610, the physical condition determination portion 322 determines whether or not a maximum value of frequency data of the PSD is not less than the determination threshold value. When the maximum value of frequency data of the PSD is less than the determination threshold value (NO in step S1610), the process of FIG. 17 is terminated. When the maximum value of frequency data of the PSD is not less than the determination threshold value (YES in step S1610), the process proceeds to step S540. Steps S540 and S550 in FIG. 17 are respectively the same as steps S540 and S550 in FIG. 5.

As described above, as with the third embodiment, by comparing frequency data of the PSD with a determination threshold value determined in advance, it is possible to detect a deteriorated physical condition of a driver at an early stage before the deteriorated physical condition of the driver progresses.

Note that the aforementioned specific embodiments mainly include the invention having the following configuration.

An aspect of the technique disclosed herein is directed to a driver's physical condition detection device for detecting a physical condition of a driver driving a vehicle. The driver's physical condition detection device includes: a vehicle detector configured to detect a change in motion of the vehicle during driving; a driver detector configured to detect a change in motion of a head of the driver; and a physical condition determination portion configured to perform a determination process of determining whether or not the physical condition of the driver is deteriorated, based on the change in motion of the head of the driver with respect to the change in motion of the vehicle during driving.

In the aforementioned configuration, the physical condition determination portion performs the determination process of determining whether or not the driver's physical condition is deteriorated, based on the change in motion of the head of the driver with respect to the change in motion of the vehicle during driving. The change in motion of the head of the driver with respect to the change in motion of the vehicle during driving is different between a stage when the driver's physical condition starts to deteriorate, and a case where the driver's physical condition is normal. According to the aforementioned configuration, it is possible to detect a deteriorated physical condition of a driver at an early stage before the deteriorated physical condition of the driver progresses.

In the aforementioned configuration, for instance, the vehicle detector may detect a change in motion of the vehicle in a left-right direction of the vehicle as the change in motion of the vehicle during driving. The driver detector may detect a change in motion of the head in the left-right direction as the change in motion of the head of the driver. The physical condition determination portion may perform the determination process, based on the change in motion of the head in the left-right direction with respect to the change in motion of the vehicle in the left-right direction.

According to the aforementioned configuration, the physical condition determination portion performs the determination process, based on the change in motion of the head in the left-right direction of the vehicle with respect to the change in motion, of the vehicle in the left-right direction. The change in motion of the head in the left-right direction with respect to the change in motion of the vehicle in the left-right direction is significantly different between a stage when the driver's physical condition starts to deteriorate, and a case where the driver's physical condition is normal, as compared with a case of a front-rear direction of the vehicle. According to the aforementioned configuration, it is possible to detect a deteriorated, physical condition of a driver at an early stage before the deteriorated physical condition of the driver progresses.

In the aforementioned configuration, for instance, the driver detector may detect an acceleration of the head of the driver, as the change in motion of the head of the driver. The physical condition determination portion may determine that the physical condition of the driver is deteriorated when a ratio of the acceleration of the head of the driver with respect to the change in motion of the vehicle during driving is not less than a predetermined value.

According to the aforementioned configuration, the physical condition determination portion determines that the physical condition of the driver is deteriorated when the ratio of the acceleration of the head of the driver with respect to the change in motion of the vehicle during driving is not less than the predetermined value. The ratio of the acceleration of the head of the driver with respect to the change in motion of the vehicle during driving is large at a stage when the driver's physical condition starts to deteriorate, as compared with a case where the driver's physical condition is normal. According to the aforementioned configuration, it is possible to detect a deteriorated physical condition of a driver at an early stage before the deteriorated physical condition of the driver progresses.

In the aforementioned configuration, for instance, the driver detector may detect a moving distance of the head of the driver, as the change in motion of the head of the driver. The physical condition determination portion may determine that the physical condition of the driver is deteriorated when the moving distance of the head of the driver with respect to the change in motion of the vehicle during driving is not less than a determination threshold value determined in advance.

According to the aforementioned configuration, the physical condition determination portion determines that the physical condition of the driver is deteriorated when the moving distance of the head of the driver with respect to the change in motion of the vehicle during driving is not less than the determination threshold value. The moving distance of the head of the driver with respect to the change in motion of the vehicle during driving is large at a stage when the driver's physical condition starts to deteriorate, as compared with a case where the driver's physical condition is normal. According to the aforementioned configuration, it is possible to detect a deteriorated physical condition of a driver at an early stage before the deteriorated physical condition of the driver progresses.

In the aforementioned configuration, for instance, the driver's physical condition detection device may further include a storage configured to store the determination threshold value which is determined in advance in such a manner that the determination threshold value increases, as the change in motion of the vehicle during driving increases.

According to the aforementioned configuration, the determination threshold value is determined in advance in such a manner that the determination threshold value increases, as the change in motion of the vehicle during driving increases. The moving distance of the head of the driver with respect to the change in motion of the vehicle during driving increases, as the change in motion of the vehicle during driving increases, both when the driver's physical condition is normal and when the driver's physical condition is deteriorated. According to the aforementioned configuration, it is possible to appropriately determine that the driver's physical condition is deteriorated.

In the aforementioned configuration, for instance, the driver's physical condition detection device may further include a frequency analyzer configured to perform frequency analysis with respect to time data to calculate frequency data. The driver detector may detect an acceleration of the head of the driver, as the change in motion of the head of the driver. The frequency analyzer may perform frequency analysis with respect to time data of the acceleration of the head of the driver to calculate frequency data of a power spectral density. The physical condition determination portion may determine that the physical condition of the driver is deteriorated when a maximum value of the frequency data of the power spectral density is larger than a reference value.

According to the aforementioned configuration, the frequency analyzer performs frequency analysis with respect to the time data of the acceleration of the head of the driver to calculate the frequency data of a power spectral density. The physical condition determination portion determines that the physical condition of the driver is deteriorated when the maximum value of frequency data of the power spectral density is larger than the reference value. The maximum value of frequency data of the power spectral density, which is calculated by performing frequency analysis with respect to the time data of the acceleration of the head of the driver, is large at a stage when the driver's physical condition starts to deteriorate, as compared with a case where the driver's physical condition is normal. According to the aforementioned configuration, it is possible to detect a deteriorated physical condition of a driver at an early stage before the deteriorated physical condition of the driver progresses.

In the aforementioned configuration, for instance, the physical condition determination portion may perform the determination process only when a magnitude of the change in motion of the vehicle during driving is not less than a predetermined threshold value.

According to the aforementioned configuration, the physical condition determination portion performs the determination process only when the magnitude of the change in motion of the vehicle during driving is not less than the predetermined threshold value. When the magnitude of the change in motion of the vehicle during driving is less than the predetermined threshold value, a significant difference regarding the change in motion of the head of the driver with respect to the change in motion of the vehicle during driving may not be obtained between a case where the driver's physical condition is normal, and a case where the driver's physical condition is deteriorated. According to the aforementioned configuration, it is possible to accurately perform the determination process of determining whether or not a driver's physical condition is deteriorated.

In the aforementioned configuration, for instance, the vehicle detector may include an acceleration sensor configured to detect an acceleration of the vehicle, as the change in motion of the vehicle during driving.

According to the aforementioned configuration, the acceleration sensor detects the acceleration of the vehicle as the change in motion of the vehicle during driving. The physical condition determination portion performs the determination process of determining whether or not the driver's physical condition is deteriorated, based on the change in motion of the head of the driver with respect to the acceleration of the vehicle. The change in motion of the head of the driver with respect to the acceleration of the vehicle is different between a stage when the driver's physical condition starts to deteriorate, and a case where the driver's physical condition is normal. According to the aforementioned configuration, it is possible to detect a deteriorated physical condition of a driver at an early stage before the deteriorated physical condition of the driver progresses.

In the aforementioned configuration, for instance, the driver's physical condition determination device may further include a memory configured to store a determination threshold value determined in advance as the reference value. In this case, the determination threshold value may be determined in advance in such a manner that the determination threshold value increases, as the change in motion of the vehicle increases.

In the aforementioned configuration, for instance, the driver's physical condition determination device may further include a storage configured to store, as the reference value, a value L times as large as an average value of power spectral density, which is calculated by the frequency analyzer (where L is a real number larger than 1) during a period until a predetermined period elapses after an ignition switch of the vehicle is turned on. For instance, L may be a real number not smaller than 2 and not larger than 3.

Another aspect of the technique disclosed herein is directed to a driver's physical condition detection method for use in a driver's physical condition detection device for detecting a physical condition of a driver driving a vehicle. The driver's physical condition detection method includes: a vehicle detecting step of detecting a change in motion of the vehicle during driving; a driver detecting step of detecting, a change in motion of a head of the driver; and a physical condition determining step of performing a determination process of determining whether or not the physical condition of the driver is deteriorated, based on the change in motion of the head of the driver with respect to the change in motion of the vehicle during driving.

According to the aforementioned configuration, in the physical condition determination step, the determination process of determining whether or not the driver's physical condition is deteriorated is performed, based on the change in motion of the head of the driver with respect to the change in motion of the vehicle during driving. The change in motion of the head of the driver with respect to the change in motion of the vehicle during driving is different between a stage when the driver's physical condition starts to deteriorate, and a case where the driver's physical condition is normal. According to the aforementioned configuration, it is possible to detect a deteriorated physical condition of a driver at an early stage before the deteriorated physical condition of the driver progresses.

This application claims the benefit of priority to Japanese Patent Application No. 2016-166123 filed on Aug. 26, 2016, the entire content of which is hereby incorporated herein by reference.

Although the present invention has been fully described by way of example with reference to the accompanying drawings, it is to be understood that various changes and modifications will be apparent to those skilled in the art. Therefore, unless otherwise such changes and modifications depart from the scope of the present invention hereinafter defined, they should be construed as being included therein.

The invention claimed is:

1. A driver's physical condition detection device for detecting a physical condition of a driver driving a vehicle, comprising:
   a frequency analyzer configured to perform frequency analysis with respect to time data to calculate frequency data;
   a vehicle detector configured to detect a change in motion of the vehicle during driving;
   a driver detector configured to detect an acceleration of a head of the driver; and
   a physical condition determination portion configured to perform a determination process of determining whether or not the physical condition of the driver is deteriorated, wherein
   the frequency analyzer performs frequency analysis with respect to time data of the acceleration of the head of the driver to calculate frequency data of a power spectral density, and
   the physical condition determination portion determines that the physical condition of the driver is deteriorated when a maximum value of the frequency data of the power spectral density is larger than a reference value, the reference value being associated with the detected change in motion of the vehicle during driving.

2. The driver's physical condition detection device according to claim 1, wherein
   the vehicle detector detects a change in motion of the vehicle in a left-right direction of the vehicle as the change in motion of the vehicle during driving,
   the driver detector detects an acceleration of the head of the driver in the left-right direction as the acceleration of the head of the driver.

3. The driver's physical condition detection device according to claim 1, wherein
   the physical condition determination portion performs the determination process only when a magnitude of the change in motion of the vehicle during driving is not less than a predetermined threshold value.

4. The driver's physical condition detection device according to claim 1, wherein
   the vehicle detector includes an acceleration sensor configured to detect an acceleration of the vehicle, as the change in motion of the vehicle during driving.

5. A driver's physical condition detection method for use in a driver's physical condition detection device for detecting a physical condition of a driver driving a vehicle, comprising:
   a frequency analyzing step of performing frequency analysis with respect to time data to calculate frequency data;
   a vehicle detecting step of detecting an acceleration of the vehicle during driving;
   a driver detecting step of detecting an acceleration of a head of the driver; and
   a physical condition determining step of performing a determination process of determining whether or not the physical condition of the driver is deteriorated, wherein
   the frequency analyzing step performs frequency analysis with respect to time data of the acceleration of the head of the driver to calculate frequency data of a power spectral density, and
   the physical condition determining step determines that the physical condition of the driver is deteriorated when a maximum value of the frequency data of the power spectral density is larger than a reference value, the reference value being associated with the detected acceleration of the vehicle during driving.

* * * * *